(12) United States Patent
Vogt et al.

(10) Patent No.: US 11,109,977 B2
(45) Date of Patent: *Sep. 7, 2021

(54) FEMORAL HIP JOINT SPACER WITH IRRIGATION DEVICE

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 56 days.

This patent is subject to a terminal disclaimer.

(21) Appl. No.: 16/743,338

(22) Filed: Jan. 15, 2020

(65) Prior Publication Data

US 2020/0222196 A1 Jul. 16, 2020

(30) Foreign Application Priority Data

Jan. 16, 2019 (DE) .......................... 102019101081.0

(51) Int. Cl.
*A61F 2/36* (2006.01)
*A61F 2/46* (2006.01)
*A61F 2/30* (2006.01)

(52) U.S. Cl.
CPC .......... *A61F 2/3609* (2013.01); *A61F 2/4675* (2013.01); *A61F 2002/30738* (2013.01); *A61F 2002/365* (2013.01); *A61F 2002/3613* (2013.01)

(58) Field of Classification Search
CPC ........ A61F 2/36; A61F 2/3609; A61F 2/3662; A61F 2/4675; A61F 2002/3613;
(Continued)

(56) References Cited

U.S. PATENT DOCUMENTS 5,681,289 A 10/1997 Wilcox et al.
6,245,111 B1 6/2001 Shaffner
(Continued)

FOREIGN PATENT DOCUMENTS

DE 102015104704 9/2016
DE 102018106705 9/2019
(Continued)

OTHER PUBLICATIONS

Office Action from corresponding German Patent Application No. 102019101081 dated Nov. 4, 2019.
(Continued)

*Primary Examiner* — Brian A Dukert
(74) *Attorney, Agent, or Firm* — Stradley Ronon Stevens and Young, LLP

(57) ABSTRACT

A femoral hip joint spacer. The spacer has a prosthesis body with a ball head, a neck, a stem and an anchoring sleeve which encloses the stem on a proximal side of the stem with a circumferential fastening area, irrigation liquid inlet and outlet openings in the body surface, at least one irrigation liquid discharge opening on a distal side of the stem and at least one irrigation liquid intake opening on the ball head or on the neck. The discharge opening is connected in a liquid-permeable manner to the inlet opening but not to the outlet opening and the intake opening is connected inside the prosthesis body in a liquid-permeable manner to the outlet opening but not to the inlet opening. A cavity open on two sides is formed inside the anchoring sleeve and connects a proximal side to a distal side of the sleeve in a liquid-permeable manner.

20 Claims, 12 Drawing Sheets

(58) Field of Classification Search
CPC .... A61F 2002/30677; A61F 2002/3068; A61F 2002/368
See application file for complete search history.

(56) References Cited

U.S. PATENT DOCUMENTS

| | | | |
|---|---|---|---|
| 8,029,498 B2 * | 10/2011 | Johnson | A61M 1/0084 604/543 |
| 8,900,322 B2 | 12/2014 | De Beaubien | |
| 2008/0058950 A1 | 3/2008 | Leonard et al. | |
| 2010/0042213 A1 | 2/2010 | Nebosky et al. | |
| 2011/0015754 A1 | 1/2011 | Leonard et al. | |
| 2013/0187310 A1 | 7/2013 | Vogt et al. | |
| 2013/0211369 A1 | 8/2013 | de Beaubien | |
| 2016/0332328 A1 | 11/2016 | Wust et al. | |
| 2018/0028320 A1 | 2/2018 | Forsell | |
| 2019/0290833 A1 | 9/2019 | Vogt et al. | |

FOREIGN PATENT DOCUMENTS

| | | |
|---|---|---|
| EP | 1991170 | 11/2008 |
| EP | 2617393 | 7/2013 |
| EP | 3542759 | 9/2019 |
| WO | 2016205077 | 12/2016 |
| WO | 2017178951 | 10/2017 |

OTHER PUBLICATIONS

European Search Report dated Jul. 31, 2020 for European Patent Application EP20151621.

* cited by examiner

FEMORAL HIP JOINT SPACER WITH IRRIGATION DEVICE

RELATED APPLICATION

This application claims the benefit of priority to German Patent Application Number DE 10 2019 101 081.0, filed on Jan. 16, 2019, the contents of which are incorporated in this application by reference.

TECHNICAL FIELD

The invention relates to a femoral hip joint spacer with an irrigation device for temporary replacement of at least one part of a hip joint, which is intended for the interim phase of two-stage septic revisions of hip joint endoprostheses. The hip joint spacer may in particular be used in two-stage septic revisions in which two or more microbial microorganisms are the cause of an infection in the hip joint endoprosthesis and the surrounding tissue.

BACKGROUND OF THE DISCLOSURE

Hip joint endoprostheses are implanted in large numbers worldwide. Unfortunately, in a small percentage of cases, hip joint endoprostheses are colonized by microbial microorganisms, particularly Gram-positive bacteria and also Gram-negative bacteria, and to a very small extent by yeasts and fungi. These microbial microorganisms, mainly typical skin microbes such as Staphylococcus aureus and Staphylococcus epidermidis, may enter a patient's body during a surgical operation (OP). It is also possible for microbial microorganisms to enter hip joint endoprostheses hematogenically. Where hip joint endoprostheses are colonized by microbial microorganisms, the surrounding bone and soft tissue also become infected and damaged by the microbial microorganisms.

The prior art primarily encompasses two treatment methods for infected hip joint endoprostheses, one-stage septic revision and two-stage septic revision. There are also a number of further treatment methods such as, for example, the application of suction/irrigation drains.

In the case of one-stage revision, within one OP first of all the infected hip joint endoprosthesis is removed, next radical debridement is performed and then a revision hip joint endoprosthesis is implanted.

In two-stage septic revisions, in a first OP the infected hip joint endoprosthesis is initially removed, then debridement is performed and thereafter a hip joint spacer is implanted. The hip joint spacer consists of a stem, a collar, a neck and a ball head and replicates hip joint endoprostheses in shape and size. The hip joint spacer is anchored to the proximal femur or respectively in the femoral canal with bone cement. The hip joint spacer remains for up to several weeks in the patient until the inflammation has subsided and the clinical inflammation markers have receded. The hip joint spacer is then removed in a second OP and a revision hip joint endoprosthesis implanted after fresh debridement.

US 2010/0042213 A1 discloses a hip joint prosthesis with a reservoir for liquid inside the implant. A hip spacer is known from WO 2017/178951 A1 which has recesses, wherein a substance for treating the bone may be introduced into the recesses. U.S. Pat. No. 6,245,111 B1 proposes a hip joint prosthesis, the surfaces of which are coated with an antibiotic. U.S. Pat. No. 5,681,289 discloses an apparatus for distributing a liquid active ingredient with the assistance of a bladder inside the apparatus. None of the indicated prostheses is suitable for producing an irrigation circuit.

The concept of using spacers provided with antibiotics is known. Hip joint spacers may be produced, on the one hand, by the OP personnel during the OP itself from polymethyl methacrylate (PMMA) bone cement powder, antibiotics and monomer liquid, for example with a spacer shape, as described for example in patents DE 10 2015 104 704 B4 or EP 2 617 393 B1. On the other hand, it is also conventional to use hip joint spacers prefabricated industrially from bone cement.

In spacers to date, antibiotics have been added to the cement powder before actual spacer production. Spacers are subsequently cast using this antibiotically modified bone cement powder and then harden by polymerization with the assistance of a monomer liquid added to the cement powder. The bone cement paste thus substantially encloses the antibiotics. Only the antibiotic particles situated in areas close to the surface are released under the action of bodily fluids, such as wound secretions. Active ingredient release is greatest at the start and then diminishes over the course of several days. Thereafter, only small quantities of the antibiotics continue to be released. The majority of the added antibiotics remains in the hardened bone cement of the spacers. In the case of spacers hitherto manufactured from bone cement, a subsequent change in the type and number of antibiotics used is not possible after spacer production or respectively after implantation. It is moreover likewise impossible to adjust a defined concentration of antimicrobially active ingredients in the wound secretions or respectively the bodily fluid surrounding the spacer.

In patent EP 1 991 170 B1 a hip joint spacer is described in which the ball head and the stem may be assembled by the user, wherein the ball head contains a first active ingredient and the stem is provided with a second active ingredient.

A further hip joint spacer is disclosed in US 2011/0015754 A1. In this spacer system, two cylindrical cavities are provided in the ball head which emerge with a narrow side at the ball surface. The two cavities are each closed with a liquid-permeable cap. Both cavities may be filled with antibiotic solutions. After implantation, the antibiotic solutions migrate through the liquid-permeable caps to the surface of the spacer. US 2019/0290833 A1 discloses an irrigatable hip joint spacer with which a liquid circuit may be produced.

In WO 2016/205077 A1 and U.S. Pat. No. 8,900,322 B2, spacers having an irrigation function are described. In the hip joint spacers described therein, a plurality of discharge openings are arranged on the outside of a spacer stem. Moreover, the openings are located in recesses, so-called valleys, of fins. The fins are used for anchoring purposes in the femoral canal and for spacing the openings from the walls of the femoral canal so that the openings cannot be covered by bone tissue. During debridement in the context of bilateral replacement, infected and necrotic tissue is extensively and radically removed. The diameter of the femoral canal may therefore vary within broad limits. Anchoring of the hip joint spacer using fins is only possible, however, if the radial dimensions of the fins correspond to the diameter of the femoral canal. Neither WO 2016/205077 A1 nor U.S. Pat. No. 8,900,322 B2 describes devices which make it possible to adapt the anchoring in accordance with the dimensions of the femoral canal. US 2019/0290833 A1 discloses a femoral hip joint spacer with an irrigation device in which irrigation liquid is conducted by two ducts from outside into the spacer and out of the spacer, in order to produce at least one irrigation liquid circuit.

In the case of two-stage septic revision, drains are also used during implantation of the hip joint spacers, these being intended to carry away wound secretions, blood and debris. The drains remain inside the patient for up to several days. The antibiotic active ingredients released by the spacer are taken up by the wound secretions and carried out via the drain. Thus, a proportion of the antimicrobial active ingredients for protecting the spacer surface from microbial colonization are lost.

SUMMARY OF THE INVENTION

It was identified, for the purposes of the present invention, that it would be desirable for the spacer surface to be surrounded by an antimicrobial active ingredient solution, the active ingredient concentration of which may be precisely adjusted and the concentration of which would be maintained for several days irrespective of wound secretion flow. It would moreover be desirable to be able to vary the type and number of microbial active ingredients even after implantation of the hip joint spacer, so as to be able to respond to microbial microorganisms only detected later, for instance. At the same time, the patient needs to be able to move the hip joint, to prevent the tendons and muscles from shortening and the muscles from degenerating and thereby to reduce rehabilitation time.

An object of the present invention thus consists of overcoming the disadvantages of the prior art. In particular, an object of the invention consists of developing a temporary femoral hip joint spacer with which a medical irrigation liquid may be used in a targeted manner in the hip region and in which the medical irrigation liquid can, if at all possible, reach the entire surface of the prosthesis body of the hip joint spacer in order to make it possible to medically treat all of the tissue adjoining the surface of the prosthesis body, apart from the direct anchoring to the femur. At the same time, the hip joint spacer is intended to allow hip joint mobility when in use in a patient.

An object of the invention is in this respect to develop an articulating hip joint spacer which is intended for the interim phase of two-stage septic hip joint endoprosthesis revisions and which has characteristics which are beneficial for this purpose. The hip joint spacer is intended to fill the space after removal of the hip joint endoprosthesis and subsequent debridement in such a way as to prevent ligament and muscle degeneration. The hip joint spacer is intended to enable the articulating spacer surface, the soft tissue surrounding the hip joint spacer and at least a proportion of the surrounding bone tissue to be irrigated continuously or indeed discontinuously with antiseptic or antibiotic irrigation liquids. The hip joint spacer can be connected to the bone tissue of the proximal femur with bone cement in such a way that exit of the irrigation liquid from the stem or in the region of the stem of the hip joint spacer and also uptake of the irrigation liquid into the hip joint spacer for drainage are not disturbed or interrupted. The nature of the hip joint spacer is furthermore intended as far as possible to be such that after completion of irrigation with the irrigation liquid, the irrigation liquid feed duct and the irrigation liquid drain duct may be removed without impairing hip joint spacer articulation.

In order to avoid circulation problems and embolisms it is standard medical practice to mobilize patients in the interim phase. It is therefore essential that the hip joint spacer can be mechanically fixed in the proximal femur. The mechanical fastening is absolutely necessary in order to avoid unwanted mechanical stressing, in particular bending stresses of the proximal femur. Otherwise, bending stresses of the femur due to non-fixed hip joint spacers can result in femur fractures.

The objects of the invention are achieved by a femoral hip joint spacer for temporary replacement of part of a hip joint, the hip joint spacer having:

a prosthesis body, the prosthesis body having a ball head with a sliding surface, a neck, the proximal side of which is connected to the ball head, a stem which is connected to the neck on a distal side of the neck which is opposite the ball head, and an anchoring sleeve which encloses the stem on a proximal side of the stem with a circumferential fastening area and which is connected to the stem, the hip joint spacer further having an irrigation liquid inlet opening in a surface of the prosthesis body, an irrigation liquid outlet opening in the surface of the prosthesis body, at least one irrigation liquid discharge opening on a distal side of the stem and at least one irrigation liquid intake opening on the ball head or on the neck, wherein the at least one irrigation liquid discharge opening is connected inside the prosthesis body in a liquid-permeable manner to the irrigation liquid inlet opening and is not connected inside the prosthesis body in a liquid-permeable manner to the irrigation liquid outlet opening, and the at least one irrigation liquid intake opening is connected inside the prosthesis body in a liquid-permeable manner to the irrigation liquid outlet opening and is not connected inside the prosthesis body in a liquid-permeable manner to the irrigation liquid inlet opening, and wherein a cavity which is open on two sides is formed inside the anchoring sleeve, which cavity connects a proximal side of the anchoring sleeve to a distal side of the anchoring sleeve in a liquid-permeable manner.

In the present patent application, the statements of direction ("proximal," "distal" and "lateral") and the statements relating to planes ("sagittal plane," "front plane" and "transverse plane") relating to the hip joint spacer are used in such a way as would be understood as a main anatomical direction or body plane when inserted into the patient. For instance, "proximal" means towards the center of the body and "distal" means remote from the center of the body.

The fastening area is provided for connecting to a femur and may preferably be introduced, for this purpose, into a proximal end of the prepared femur or respectively into the femoral canal.

The anchoring sleeve preferably has a closed lateral surface. Likewise, the fastening area preferably encloses the stem completely.

The hip joint spacer can be made of metal, plastic, elastomers, ceramic or combinations of these materials.

The hip joint spacer is preferably suitable for the application of at least one antibiotic and/or antimycotic active ingredient which prevents or impairs polymerization or free-radical polymerization of PMMA. In particular, the hip joint spacer is suitable for the application of rifampicin and metronidazole.

The prosthesis body is preferably in one piece. The prosthesis body is particularly preferably made in one piece from a biocompatible material such as PMMA, wherein the PMMA very particularly preferably contains at least one antibiotic and/or antimycotic which may be detached from the PMMA.

Alternatively, the hip joint spacer can be formed in two pieces and have a head part comprising the ball head and a stem which may be detached from the head part, wherein the anchoring sleeve is undetachably connected to the stem.

The at least one irrigation liquid discharge opening and the at least one irrigation liquid intake opening are preferably arranged in the surface of the prosthesis body.

The hip joint spacer can have a first tubular and liquid-permeable connector for draining the irrigation liquid from the prosthesis body, wherein the first connector is connected or connectable in a liquid-permeable manner to the irrigation liquid outlet opening, and the hip joint spacer has a second tubular and liquid-permeable connector for feeding a medical irrigation liquid into the prosthesis body, wherein the second connector is connected or connectable in a liquid-permeable manner to the irrigation liquid inlet opening.

As a result, the irrigation liquid may be fed into the prosthesis body and drained from the prosthesis body in a simple manner.

The irrigation liquid can theoretically also initially be introduced through the second connector and drained through the first connector and then through the first connector and drained through the second connector. The hip joint spacer is then operated in alternating manner. It is preferred according to the invention, however, for the hip joint spacer to be operated or respectively operable in just one flow direction of the irrigation liquid.

The first tubular liquid-permeable connector is preferably a hose with an adapter or another connection.

The second tubular liquid-permeable connector is preferably a hose with an adapter or another connection.

In hip joint spacers according to the invention having the first and the second connectors, the first connector on the side facing away from the connection to the irrigation liquid inlet opening and the second connector on the side facing away from the connection to the irrigation liquid outlet opening in each case have an adapter, in particular in each case a luer lock adapter.

In hip joint spacers according to the invention, a first valve element is arranged in the first connector or in the irrigation liquid outlet opening, the valve element preventing backflow of the irrigation liquid into the first connector, and/or a second valve element is arranged in the second connector or in the irrigation liquid inlet opening, the valve element preventing backflow of the irrigation liquid into the second connector. The first and/or the second valve element (s) can be selected from a non-return valve, a ball valve with spring, a lip valve, a Bunsen valve or a plate valve.

This configuration makes it possible to predefine a circulating circuit of the medical irrigation liquid. In addition, backflow of the medical irrigation liquid used is thus prevented.

According to a preferred further embodiment of the present invention, the at least one irrigation liquid discharge opening and the at least one irrigation liquid intake opening are arranged in the surface of the prosthesis body outside the circumferential fastening area.

This configuration ensures that the irrigation liquid exiting from the at least one irrigation liquid discharge opening or respectively the irrigation liquid streaming in through the at least one irrigation liquid intake opening cannot impair the connection with the femur and that, on the other hand, the cement which is used to fasten the hip joint spacer to the femur or respectively in the femoral canal, does not undesirably close one or more of the at least one irrigation liquid discharge opening and/or the at least one irrigation liquid intake opening.

The irrigation liquid inlet opening and/or the irrigation liquid outlet opening can be arranged on the ball head or on the neck of the prosthesis body, wherein the irrigation liquid inlet opening and/or the irrigation liquid outlet opening is/are preferably arranged on a lateral side of the neck of the prosthesis body.

At these points of the prosthesis body, the connecting hoses may be particularly easily connected to the prosthesis body without impairing the function of the prosthesis body and without making the movement of the joint difficult.

The stem can be shaped like a hollow cylinder, wherein a duct is formed inside the stem, which connects the at least one irrigation liquid discharge opening to the irrigation liquid inlet opening in a liquid-permeable manner.

In this way, the irrigation liquid inside the stem may be conducted from the irrigation liquid inlet opening to the at least one irrigation liquid discharge opening on the distal side of the stem.

Preferably, the fastening area is delimited so that the fastening area is suitable for accommodating bone cement paste.

Alternatively, the fastening area can be delimited by two circumferential crosspieces extending up out of the surface of the prosthesis body on a proximal side and on a distal side of the anchoring sleeve, wherein the fastening area is suitable for accommodating bone cement paste within the crosspieces.

According to a further alternative, the fastening area can be delimited by one circumferential crosspiece extending up out of the surface of the prosthesis body on a distal side of the anchoring sleeve and one circumferential collar extending up out of the surface of the prosthesis body on a proximal side of the anchoring sleeve, wherein the fastening area is suitable for accommodating bone cement paste within the crosspiece and the collar.

Thanks to these three alternative embodiments, a delimited and thereby specific region may be used for fastening the prosthesis body in the femoral canal. When the hip joint spacer is used correctly, this may prevent the irrigation liquid inlet opening and the irrigation liquid outlet opening as well as the at least one irrigation liquid discharge opening and the at least one irrigation liquid intake opening from being covered with bone cement and their function thereby being impaired. It is in particular possible to prevent the hardened bone cement, with which the hip joint spacer is anchored in the femur, from preventing the first and second connectors from being pulled away or detached from the prosthesis body.

In order to optimize the complete treatment, a first irrigation liquid discharge opening of the at least one irrigation liquid discharge opening can be arranged at the distal end of the stem.

In this way, it is ensured that the irrigation liquid can also irrigate at the distal end of the stem with the medical irrigation liquid such that thorough irrigation of the femur may also proceed to the achievable depth.

A second irrigation liquid discharge opening can be arranged on the proximal side of the ball head, wherein the one first irrigation liquid discharge opening and the second irrigation liquid discharge opening are connected inside the prosthesis body in a liquid-permeable manner to the irrigation liquid inlet opening.

The second irrigation liquid discharge opening ensures that the ball head is also irrigated on its sliding surface to a greater extent with the medical irrigation liquid.

The at least one irrigation liquid intake opening can be arranged on the neck of the prosthesis body and/or on the distal side of the ball head.

In this way, the flow of the irrigation liquid is directed at a region which is accessible from the outside, and which is important for treatment. The irrigation liquid may flow through the cavity in the anchoring sleeve and thus flow around the entire prosthesis body. In addition, thanks to this configuration the at least one irrigation liquid intake opening can be arranged tightly or even at the same location as the irrigation liquid outlet opening so that no ducts or only a very short duct is/are necessary to connect the at least one irrigation liquid intake opening to the irrigation liquid outlet opening.

The at least one irrigation liquid intake opening and the irrigation liquid outlet opening may preferably be formed in a joint blind hole in the surface of the prosthesis body.

Furthermore, the anchoring sleeve can be arranged between the at least one irrigation liquid discharge opening and the at least one irrigation liquid intake opening so that when the circumferential fastening area is connected in a fluid-tight manner to a surrounding femoral canal, the irrigation liquid may only flow through the cavity which is open on two sides from the at least one irrigation liquid discharge opening to the at least one irrigation liquid intake opening.

This configuration ensures that the irrigation liquid can also reach all the surfaces of the prosthesis body even when the circumferential fastening area is completely connected to the femoral canal.

A self-sealing coupling can be arranged at the irrigation liquid inlet opening inside the prosthesis body or at the surface of the prosthesis body and a self-sealing coupling can be arranged at the irrigation liquid outlet opening inside the prosthesis body or at the surface of the prosthesis body, wherein connectors are preferably detachably connected or connectable to the irrigation liquid inlet opening and the irrigation liquid outlet opening.

In this way, the irrigation liquid inlet opening and the irrigation liquid outlet opening or respectively the liquid ducts therebehind close automatically if a connector such as, in particular, the first connector or the second connector is pulled away or separated from the prosthesis body. As a result, one (or more) fluid-conducting connection(s) present in the prosthesis body may be closed if no more irrigation liquid is to be conducted through the hip joint spacer.

According to a further embodiment of the present invention, the sum of the cross-sectional areas of all of the at least one irrigation liquid intake opening together to be at least as great as the cross-sectional area of the irrigation liquid inlet opening and/or the sum of the cross-sectional areas of all of the at least one irrigation liquid discharge opening to be at least as great as the cross-sectional area of the irrigation liquid outlet opening.

In this way, a dynamic pressure inside the prosthesis body can be avoided.

Preferably, a first valve is arranged in a first duct within the prosthesis body, which connects the at least one irrigation liquid intake opening in a liquid-permeable manner to the irrigation liquid outlet opening. The first valve is openable solely by applying a vacuum at the irrigation liquid outlet opening and prevents backflow of the irrigation liquid into the first duct.

A second valve is arranged in a second duct within the prosthesis body, which connects the at least one irrigation liquid discharge opening in a liquid-permeable manner to the irrigation liquid inlet opening. The second valve is openable solely by applying a vacuum at the irrigation liquid inlet opening and prevents backflow of the irrigation liquid into the second duct.

Backflow of the medical irrigation liquid may also be prevented by these two alternatives. It may additionally be ensured in this way that an exchange of contained irrigation liquid with surrounding liquids still takes place without the connector.

The irrigation liquid inlet opening, the irrigation liquid outlet opening, the at least one irrigation liquid discharge opening and the at least one irrigation liquid intake opening and the liquid-permeable connections can be formed in the prosthesis body, wherein the prosthesis body is preferably made of plastic, metal, ceramic, glass ceramic, bone cement or a combination thereof.

A compact structure is thereby achieved and the prosthesis body externally resembles a conventional femoral hip joint spacer, apart from the openings.

The irrigation liquid inlet opening and the irrigation liquid outlet opening can be arranged in a lateral surface of the neck and/or the distal side of the ball head.

This configuration makes feed and drainage of the irrigation liquid into and out of the hip joint spacer anatomically easy and comfortable to put in place. At the lateral side surface, the connector connected to the irrigation liquid inlet opening and the irrigation liquid outlet opening is particularly untroublesome during walking and is also particularly readily accessible.

The free duct cross-section of the cavity of the anchoring sleeve, which is open on two sides, can be as large as or larger than the free duct cross-section in the stem.

Furthermore, the cavity which is open on two sides can extend at least in certain areas parallel to the longitudinal axis of the stem and can be delimited by the outer lateral surface of the stem and the internal wall of the anchoring sleeve.

These two alternatives ensure that the irrigation liquid can flow without an impeding dynamic pressure though the cavity of the anchoring sleeve, which is open on two sides, even if tissue residue is also carried along. To this end, the free duct cross-section of the cavity of the anchoring sleeve, which is open on two sides, is preferably larger than the free duct cross-section in the stem, particularly preferably at least 50% larger than the free duct cross-section in the stem, very particularly preferably at least double the size of the free duct cross-section in the stem. The free duct cross-section in the stem corresponds to the free cross-section of the duct for the irrigation liquid inside the stem, which leads to the at least one irrigation liquid discharge opening.

Moreover, the anchoring sleeve can have a closed lateral surface or the anchoring sleeve can have a notch which is arranged parallel to the longitudinal axis of the hollow cylinder-shaped stem.

In this way, either a complete fastening is made possible or the outer circumference of the anchoring sleeve can be adapted to the femoral canal of the femur to be treated.

According to a preferred embodiment of the present invention, a collar is arranged on the distal side of the ball head and distally from the irrigation liquid inlet opening and the irrigation liquid outlet opening as well as between the ball head and the anchoring sleeve, wherein the collar runs around the proximal end of the anchoring sleeve, wherein the at least one irrigation liquid discharge opening is preferably arranged on the side facing distally away from the collar on the stem.

The collar may prevent bone cement for anchoring the prosthesis body in the femoral canal from closing a proximal opening of the cavity of the anchoring sleeve, which is open on two sides, or reducing the free diameter thereof.

The ball head can have at least one liquid-permeable canal which emerges into at least one irrigation liquid outlet opening on the surface of the ball head and which is connected to the irrigation liquid inlet opening in a liquid-permeable manner.

Further, the outer lateral surface of the anchoring sleeve can have a rubbery-elastic coating.

In this way, a particularly robust and/or anatomically adapted connection with the femur can be produced.

Furthermore, the outer lateral surface of the anchoring sleeve can have a structured surface for press-fit anchoring or for anchoring of polymethyl methacrylate bone cement.

In this way as well, a particularly robust and/or anatomically adapted connection with the femur can be produced.

Furthermore, the anchoring sleeve can taper in the distal direction, to preferably converge conically in the distal direction.

In this way, the anchoring sleeve is anatomically better adapted to the femoral canal. In addition, a more robust connection with the femur can thus be produced.

The anchoring sleeve can be sheathed by a separate hollow cylinder-shaped rubbery-elastic sleeve, wherein this component preferably has a collar on the proximal side.

This configuration ensures a robust connection with the femur. In addition, the collar may prevent the bone cement paste for connecting with the femur from flowing out via the anchoring sleeve and thus closing the cavity, which is open on two sides, on one side or reducing the free cross-section.

One of the at least one irrigation liquid intake openings can be formed as an irrigation liquid outlet opening, wherein, to this end, a fastener for detachably connecting a tubular and liquid-permeable connector is preferably arranged in the irrigation liquid intake opening for draining the irrigation liquid from the prosthesis body, wherein the irrigation liquid outlet opening cannot be closed by the connected connector.

In this way, a simpler construction can be achieved which does not require any ducts or only requires a simpler duct in the prosthesis body. If only one irrigation liquid intake opening is provided, this may be designed as a blind hole in which the connector may be detachably connected.

Preferably, the cavity of the anchoring sleeve, which is open on two sides, within the prosthesis body is not connected in a liquid-permeable manner to the irrigation liquid inlet opening and preferably within the prosthesis body also is not connected to the irrigation liquid outlet opening.

This configuration ensures that the irrigation is effected in the region of the tissue to be treated and the cavity for transferring the irrigation liquid from the distal stem of the prosthesis body to the proximal ball head of the prosthesis body can be effected through the circumferential fastening area.

The invention is based on the surprising recognition that the surface of a hip joint spacer can be irrigated completely when an anchoring sleeve is simultaneously and completely connected to the femur around its entire circumference by a cavity in the anchoring sleeve, which is open on two sides. Thanks to the cavity of the sleeve, which is open on two sides, a flow of the irrigation liquid may be conducted through the cavity, which is open on two sides, which may be guided from a distal side of the hip joint spacer (on the stem) up to a proximal side of the hip joint spacer on the ball head (or vice versa). Thanks to the at least one irrigation liquid intake opening and the at least one irrigation liquid discharge opening as well as the irrigation liquid inlet opening and the irrigation liquid outlet opening, a temporary hip joint spacer is provided for continuous irrigation of a cavity in the body of a patient in that suitable openings for the irrigation liquid are present at the surface of the prosthesis body of the hip joint spacer and suitable ducts for the irrigation liquid are present inside the prosthesis body, and in that two externally accessible connectors are connected or connectable, through which the medical irrigation liquid may be fed from outside into the prosthesis body and the used irrigation liquid may be drained back out of the prosthesis body. With the hip joint spacer according to the invention, both a distal and a proximal side of the prosthesis body may be irrigated by a connected circuit of the irrigation liquid due to the anchoring sleeve having the cavity which is open on two sides, without the fastening area of the hip joint spacer, which is used to connect to the femur, having to be flowed around by the irrigation liquid.

The hip joint spacer according to the invention may advantageously be used in the context of two-stage septic revisions, in which an infection with two or more microbial microorganisms and in particular with problematic microorganisms is present. It is particularly advantageous for the hip joint spacer and the surrounding soft tissue and at least in part also the surrounding bone tissue to be irrigated with antibiotically active solutions, such as antibiotics and also antiseptics or in specific cases with antimycotics, wherein the type and number of the active ingredients and above all the concentration of the antimicrobial active ingredients in the irrigation solution (the medical irrigation liquid) may be precisely adjusted. By suctioning the irrigation liquid away, it is also possible for the residence time of the antimicrobial irrigation liquid in the patient to be precisely adjusted. This precise adjustment makes it possible to ensure irrigation around the surface of the hip joint spacer for several days with precisely pre-adjusted concentrations of antimicrobial active ingredients in the irrigation liquid. In this way, protection from microbial recolonization of the surfaces of the hip joint spacer is markedly reduced compared with the hip joint spacers hitherto made from antibiotic-containing bone cement. After antibiotic irrigation, it is possible to irrigate the surface of the hip joint spacer and the surrounding tissue with active ingredient-free irrigation liquids, thereby removing residues of the antimicrobial active ingredients. The development of resistance as a result of persistent active ingredient residues is therefore extremely unlikely.

It is moreover advantageous for the irrigation liquids to be able to contain antimicrobial active ingredients which cannot normally be integrated into the hip joint spacers made from bone cement because they would disturb or respectively prevent free-radical polymerization of the bone cement paste. The active ingredients rifampicin and metronidazole are examples thereof.

When the clinical parameters reveal that the infection or respectively inflammation is receding, then the connector may be removed from the hip joint spacer. The connector is to this end advantageously connected by an external thread or via a bayonet closure or via a plug-type closure to the irrigation liquid inlet opening and the irrigation liquid outlet opening, or respectively in each case by a mating fastening element, matching the fastening element on the connector, in or on the irrigation liquid inlet opening and the irrigation liquid outlet opening.

Preferably, the irrigation liquid inlet opening and the irrigation liquid outlet opening terminate flush with the surface of the hip joint spacer once the connector has been removed, in order to prevent irritation of the surrounding soft tissue.

An exemplary hip joint spacer according to the invention may be composed of:

A) a ball head with a sliding surface,

B) a hollow cylinder-shaped stem which is connected by a neck to the ball head,

C) an irrigation liquid inlet opening which is arranged below (distally) the ball head and which is connected in a liquid-permeable manner to the hollow cylinder-shaped stem, D) a first hose having a first connecting element, wherein the irrigation liquid may be introduced through the first hose into the irrigation liquid inlet opening and the first connecting element detachably connects the first hose to the irrigation liquid inlet opening, E) at least one irrigation liquid discharge opening for the irrigation liquid, which is arranged at a distal end of the stem, F) an anchoring sleeve which is arranged beneath the ball head and the irrigation liquid inlet opening and which encloses the hollow cylinder-shaped stem, wherein the cross-sectional area of the anchoring sleeve is smaller than the cross-section of the hollow cylinder-shaped stem and wherein the anchoring sleeve is connected to the stem, G) a cavity extending parallel to the longitudinal axis of the hollow cylinder-shaped stem, which is delimited by the outer lateral surface of the stem and the internal wall of the anchoring sleeve, and H) a second hose having a second connecting element, wherein the irrigation liquid may be drained through the second hose from an irrigation liquid outlet opening from the hip joint spacer and the second connecting element detachably connects the second hose to the irrigation liquid outlet opening.

The hip joint spacer may be made of plastic, metal, ceramic, glass ceramic and combinations thereof. The spacer may advantageously be made from a metal core, produced by selective laser melting (SLM), and a casing of bone cement arranged therearound. It is also possible to make the entire hip joint spacer of metal, such as for example stainless steel and titanium alloys, by SLM Stainless steel 1.4404 and titanium alloy $Ti_6Al_4V$ are preferred in this case.

BRIEF DESCRIPTION OF THE DRAWING

The disclosure is best understood from the following detailed description when read in connection with the accompanying drawing. Further exemplary embodiments of the invention are explained below with reference to twelve schematically depicted figures, but without thereby restricting the invention. In the figures.

DETAILED DESCRIPTION OF THE DISCLOSURE

Figure 1:
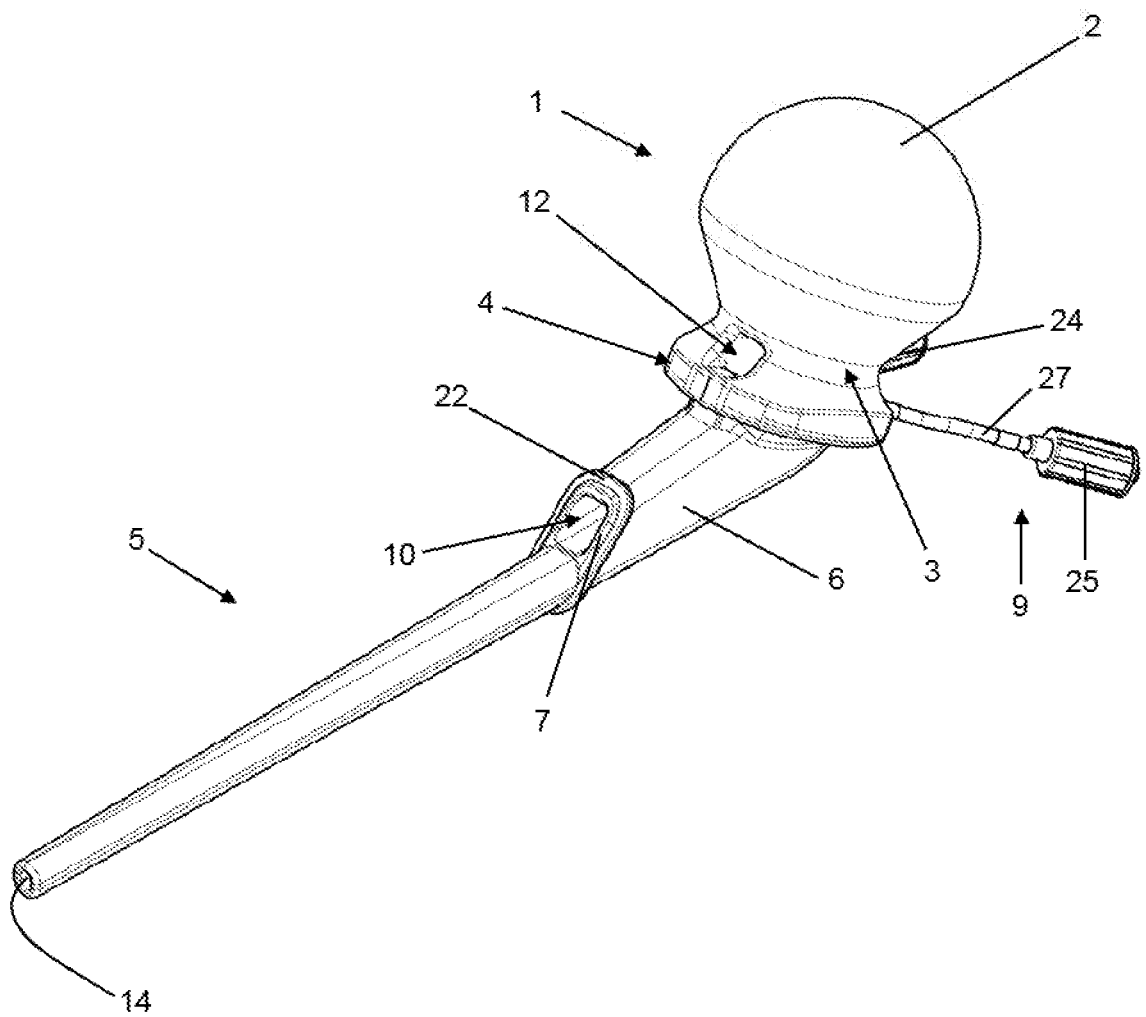
FIG. 1 is a schematic perspective external view of a first exemplary hip joint spacer according to the invention with an irrigation device.
Figure 2:
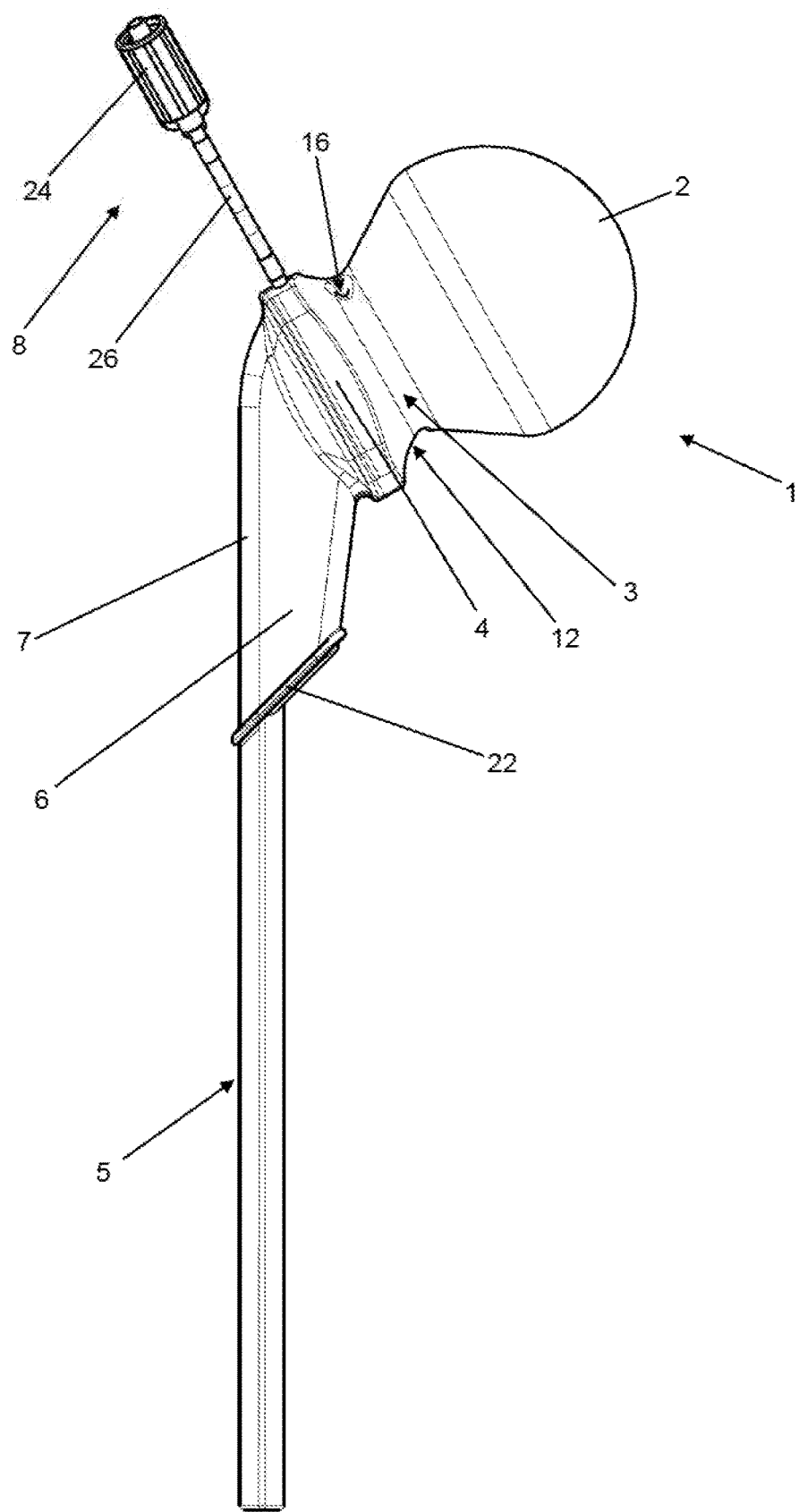
FIG. 2 is a schematic perspective side view of the first hip joint spacer according to the invention illustrated in FIG. 1.
Figure 3:
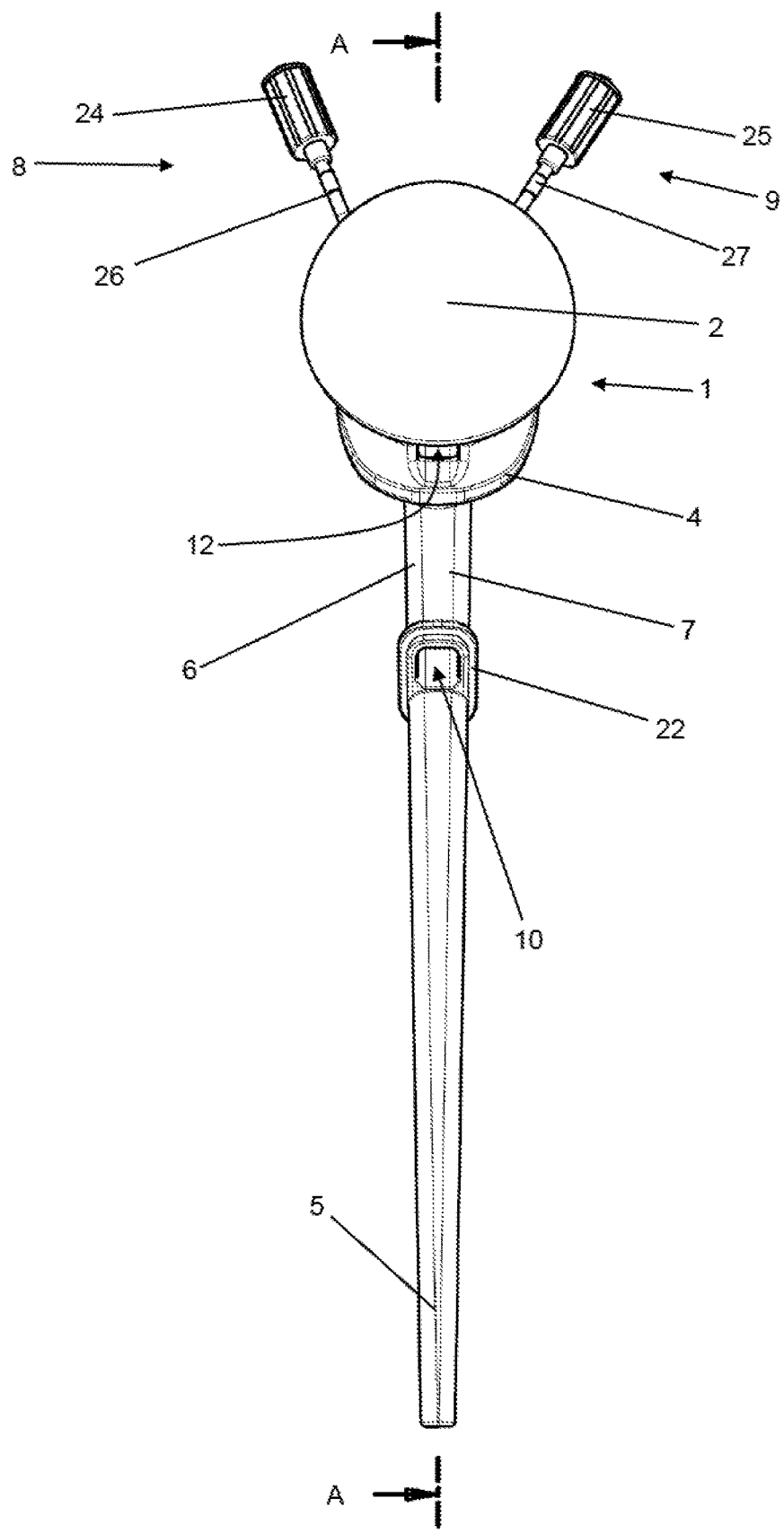
FIG. 3 is a schematic perspective external view of the first hip joint spacer according to the invention illustrated in FIGS. 1 and 2 but on another side.

FIGS. 1 to 6 show depictions of a first exemplary embodiment of a hip joint spacer according to the invention having an irrigation device. The femoral hip joint spacer (i.e., the hip joint spacer replicating the joint head of the femur and intended to be fastened to the femur) has a ball head 1 with a sliding surface 2 on the proximal side. The sliding surface 2 can lie when inserted (i.e., when inserted into the patient) against the hip joint socket and so form part of the hip joint. On the distal side opposite the sliding surface 2, the ball head 1 may be connected to a collar 4 via a neck 3. The neck 3 is preferably thinner than the ball head 1 and the collar 4. On the distal side of the collar 4 a stem 5 may be attached, which extends in the distal direction. In order to fasten the hip joint spacer in the femur, a circumferential fastening area 6 may be provided on an anchoring sleeve 7, which surrounds or respectively encloses the stem 5 on its proximal side. With the circumferential fastening area 6, a connection of the hip joint spacer in a canal of a femur may be effected with the aid of bone cement paste as the "adhesive". The ball head 1, the neck 3, the collar 4, the stem 5 and the anchoring sleeve 7 may form a prosthesis body of the hip joint spacer. The prosthesis body largely corresponds in its external shape to the external shape of known hip joint spacers, apart from the anchoring sleeve 7.

Unlike with known hip joint spacers, on one side of the first exemplary hip joint spacer a first tubular connector 8 can be fastened to an irrigation liquid outlet opening and a second tubular connector 9 can be fastened to an irrigation liquid inlet opening. The irrigation liquid inlet opening and the irrigation liquid outlet opening may lead into the inside of the prosthesis body and are arranged on the collar 4. The first tubular connector 8 and the second tubular connector 9 may be liquid-permeable, such that a medical irrigation liquid may be passed through the second tubular connector 9 into the prosthesis body and a liquid may be drained out of the prosthesis body through the first tubular connector 8. The first connector 8 may be detachably connected to the irrigation liquid outlet opening and the second connector 9 may be detachably connected to the irrigation liquid inlet opening.

The anchoring sleeve 7 may have a distal opening 10 which points in the direction of the distal end of the stem 5, and may have a proximal opening which leads in the direction of the ball head 1. The proximal opening 12 may stretch from the collar 4 right into the neck 3.

At the distal end of the stem 5 an irrigation liquid discharge opening 14 may be arranged and on the neck 3 an irrigation liquid intake opening 16 may be arranged. The anchoring sleeve 7 may be arranged between the irrigation liquid discharge opening 14 and the irrigation liquid intake opening 16.

The fastening area 6 may be delimited on the distal side by a circumferential crosspiece 22 and on the proximal side of the fastening area 6 by the collar 4. The crosspiece 22 may extend up out of the surface of the anchoring sleeve 7 and delimit the anchoring sleeve 7 on its distal side. The crosspiece 22 may be construed to be part of the prosthesis body. The aforementioned crosspiece 22 and the collar 4 may prevent bone cement paste from penetrating, or at least hinder the paste from penetrating, outside the fastening area 6 on fastening of the hip joint spacer to the femur and thereby closing or impeding the irrigation liquid discharge opening 14, the irrigation liquid intake opening 16, the irrigation liquid inlet opening and the irrigation liquid outlet opening or respectively undesirably cementing firm the first connector 8 or the second connector 9 on the prosthesis body. The collar 4 may be designed as a crosspiece protruding from the proximal end of the anchoring sleeve 7 so that the circumferential fastening area 6 is delimited on the proximal side and on the distal side by a protruding crosspiece.

The first connector 8 may have a luer lock adapter 24 and a short, flexible hose 26. The second connector 9 likewise has a luer lock adapter 25 and a short, flexible hose 27. In this way, the hip joint spacer may be connected by the second connector 9 via the luer lock adapter 25 to a source of a medical irrigation liquid with a pump (not shown) and the first connector 8 may be connected via the luer lock adapter 24 to a collecting vessel and optionally likewise a pump (not shown).

Figure 4:
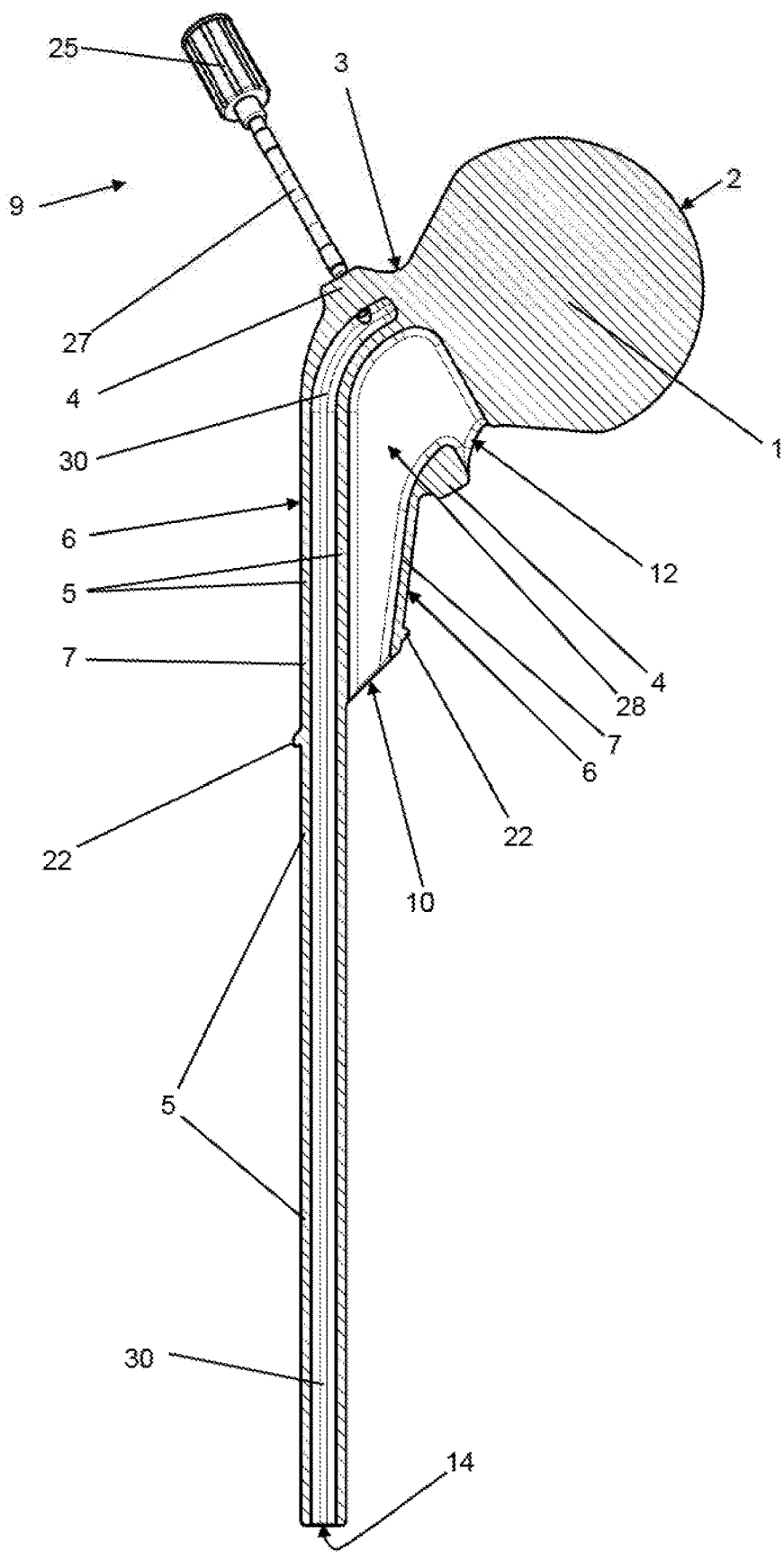
FIG. 4 is a schematic cross-sectional view of the first hip joint spacer according to the invention corresponding to section A in FIG. 3.
Figure 5:
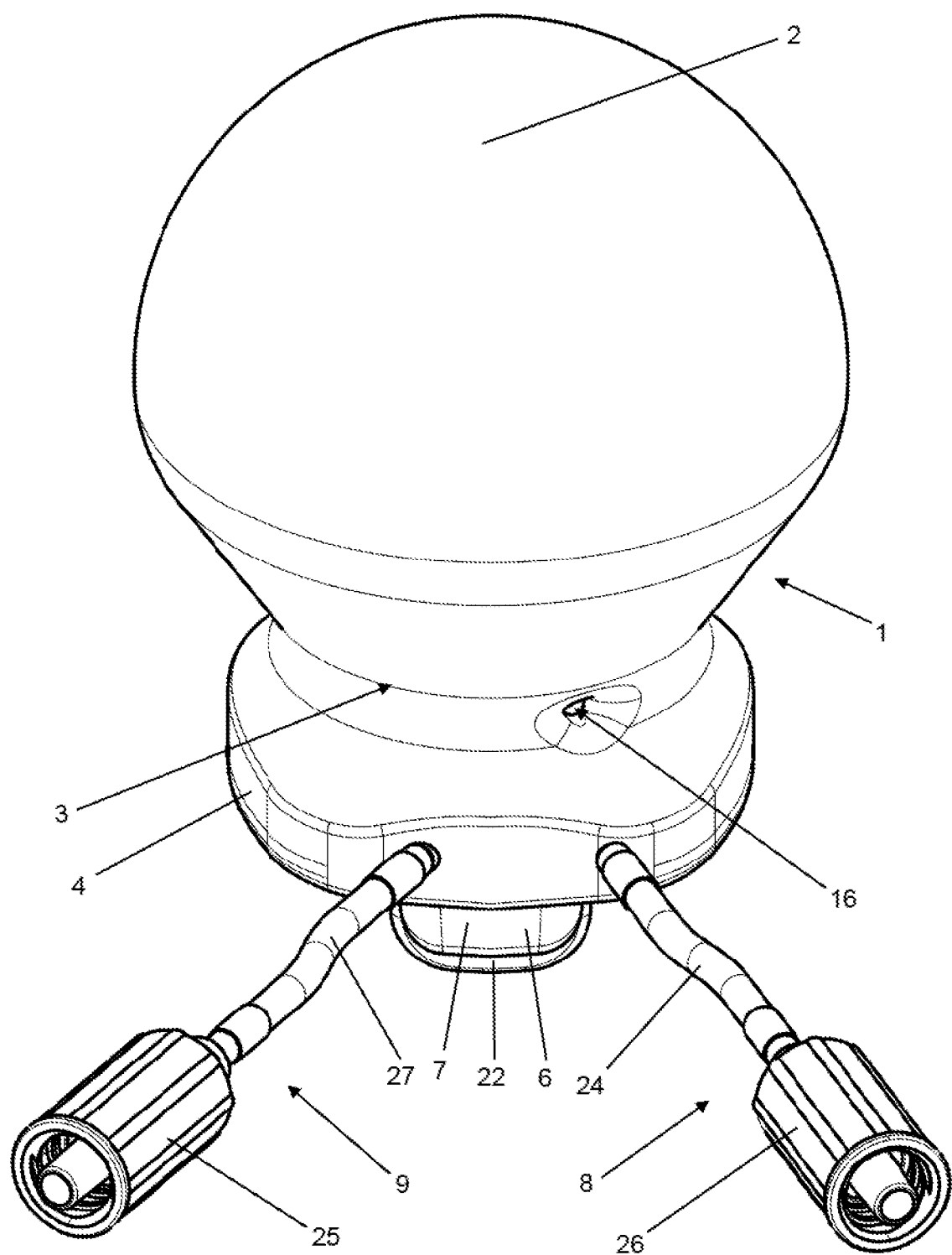
FIG. 5 is a further schematic external view of the first hip joint spacer according to the invention illustrated in FIGS. 1 to 4.
Figure 6:
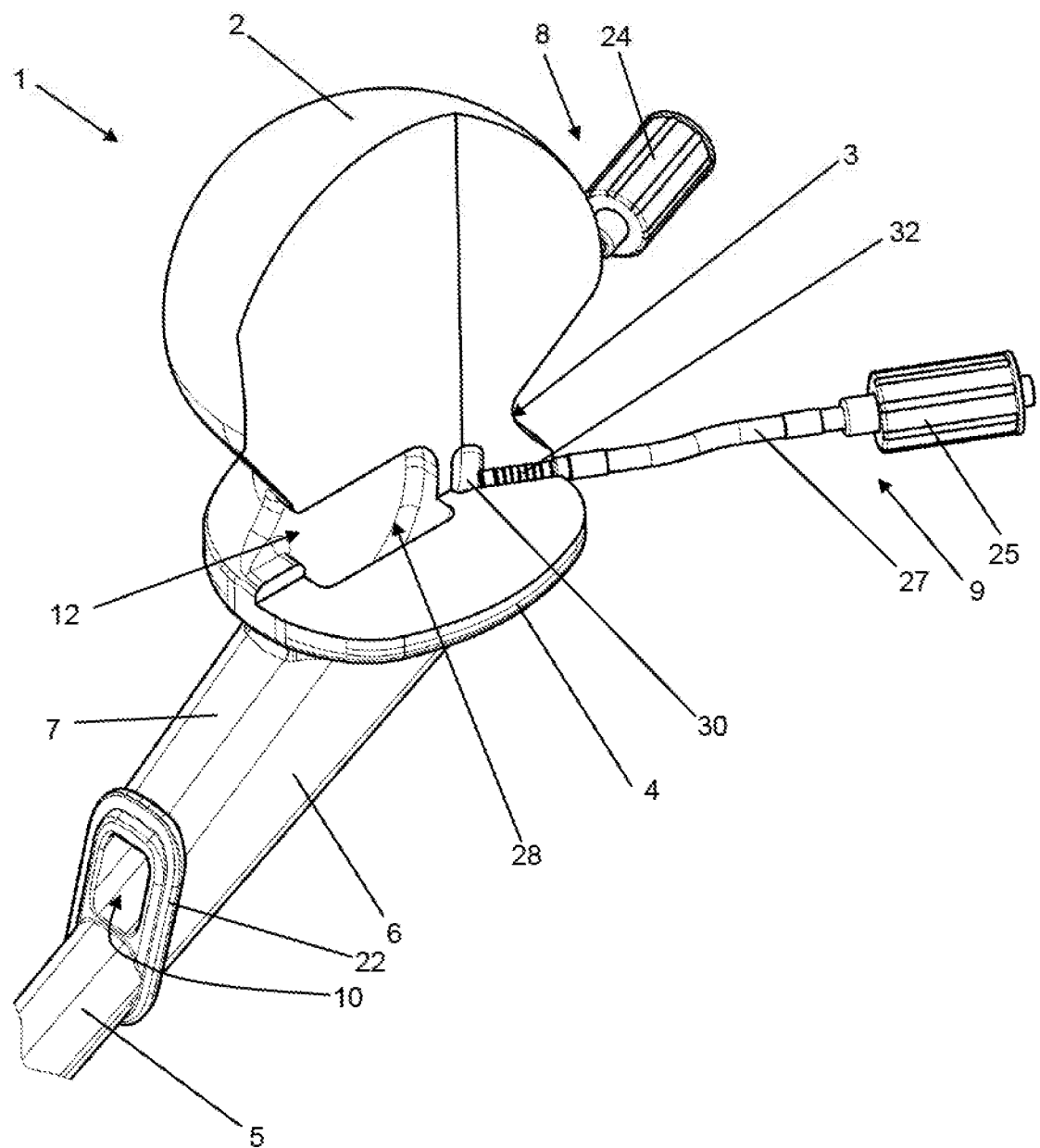
FIG. 6 is a schematic partial sectional view of a proximal section of the first hip joint spacer according to the invention illustrated in FIGS. 1 to 5.

In the cross-sectional view according to FIG. 4 and the partial sectional view according to FIG. 6, a cavity 28 can be seen, which may be delimited by the internal walls of the anchoring sleeve 7 and the external walls of the stem 5 inside the anchoring sleeve 7. The cavity 28 may connect the distal opening 10 to the proximal opening 12. As a result, the irrigation liquid can flow out of the irrigation liquid discharge opening 14, subsequently flow along the surface of the stem 5, then flow through the distal opening 10 into the cavity 28, through the cavity 28 and flow out the proximal opening 12 and flow from there over the surface of the neck 3 and of the ball head 1 to the irrigation liquid intake opening 16. The used irrigation liquid may subsequently be sucked in through the irrigation liquid intake opening 16 back into the prosthesis body. Thanks to the anchoring sleeve 7 having the cavity 28 which is open on two sides at the distal opening 10 and the proximal opening 12, the medical irrigation liquid can therefore reach the surface of the prosthesis body both on the stem 5 and on the ball head 1. As a result, it is sufficient to provide one irrigation liquid discharge opening 14 and one irrigation liquid intake opening 16, in order to be able to reach the surfaces of the prosthesis body which are achievable with the medical irrigation liquid and to be able to treat them therewith. If there is more than one irrigation liquid discharge opening 14 and more than one irrigation liquid intake opening 16, however, the connection of the two sides via the cavity 28 ensures that an exchange of liquid is possible on both sides of the prosthesis body. This prevents a malfunction and makes possible uniform treatment. At the same time, the anchoring sleeve 7 and the fastening area 6 may be completely used for cementing, i.e., for anchoring the hip joint spacer in a canal of a femur and thus make possible a particularly robust connection with the femur.

In the cross-sectional view according to FIG. 4 and the partial sectional view according to FIG. 6, it may additionally be seen how the irrigation liquid inlet opening may be connected to the irrigation liquid discharge opening 14 inside the prosthesis body via a duct 30 inside the stem 5. The stem 5 forms a hollow cylinder. As can be very clearly seen in particular in FIG. 4, the free duct cross-section of the cavity 28 may be approximately three times larger than the free duct cross-section of the duct 30. Similarly, the irrigation liquid intake opening 16 may be connected inside the prosthesis body by a separate second duct (not shown) to the irrigation liquid inlet opening.

The prosthesis body may be made substantially of a plastic material, preferably of a bone cement, such as a PMMA plastic which may be loaded with an antibiotic or with a plurality of antibiotics.

The duct 30 may establish a liquid-permeable connection between the irrigation liquid inlet opening and the irrigation liquid discharge opening 14. The first duct 30 and the second duct, which connects the irrigation liquid intake opening 16 inside the prosthesis body to the irrigation liquid outlet opening, may be separated from one another inside the prosthesis body, so that no fluid connection exists between the duct 30 and the second duct inside the prosthesis body.

A coupling element 32 may be arranged on the hose 27 of the second connector 9, which coupling element makes possible a detachable connection of the hose 27 to the irrigation liquid inlet opening. A fluid-tight connection to the irrigation liquid inlet opening may be produced with the coupling element 32.

A valve element (not shown) may be provided in the second duct, directly in front of the irrigation liquid outlet opening, the valve element allowing outflow of liquid from the second duct through the irrigation liquid outlet opening out of the prosthesis body into the first connector 8 and preventing backflow from the first connector 8 into the second duct. The first connector 8 may be connected to the irrigation liquid outlet opening via a detachable connecting element.

A valve element (not shown) can be provided in the duct, directly in front of the irrigation liquid inlet opening, the valve element allowing inflow of the medical irrigation liquid into the duct 30 through the irrigation liquid inlet opening into the prosthesis body and preventing backflow from the duct 30 into the second connector 9. The second connector 9 may be connected to the irrigation liquid inlet opening via the coupling element 32.

The first connector 8 and the second connector 9 may be detached from the prosthesis body by pulling away or unscrewing. To this end, liquid-permeable mating fastening elements may be provided in the ducts 30 in the prosthesis body. The mating fastening elements may for example be made from sleeves with internal threads, into which the coupling element 32 having an external thread has been or may be screwed.

In the inserted state, the femoral hip joint spacer may be used as follows for irrigation: a medical irrigation liquid with a composition adapted to the patient's needs, such as for example a sterile Ringer's solution with a mixture of suitable antibiotics, is fed through the second connector 9 into the prosthesis body. The medical irrigation liquid may flow through the hose 27 and through the duct 30 through the prosthesis body and exit through the irrigation liquid discharge opening 14 at the distal end of the stem 5 out of the prosthesis body. The irrigation liquid may subsequently flow along the surface of the hip joint spacer from the first irrigation liquid discharge opening 14 through the cavity 28 in the anchoring sleeve 7 to the irrigation liquid intake opening 16. The regions therebetween may be irrigated with a film of the medical irrigation liquid. The used irrigation liquid may re-enter the prosthesis body at the irrigation liquid intake opening 16 and may flow through the second duct 32 to the irrigation liquid outlet opening. From there it may be removed by suction from the prosthesis body through the first connector 8 and the used irrigation liquid may subsequently be disposed of or collected.

If no further irrigation is to take place, the connectors 8, 9 may be separated from the prosthesis body and the remaining hip joint spacer may also be used like a normal hip joint spacer. Provision may preferably be made for the irrigation liquid inlet opening and the irrigation liquid outlet opening to close automatically on pulling or screwing the connectors 8, 9 off the prosthesis body.

Figure 7:
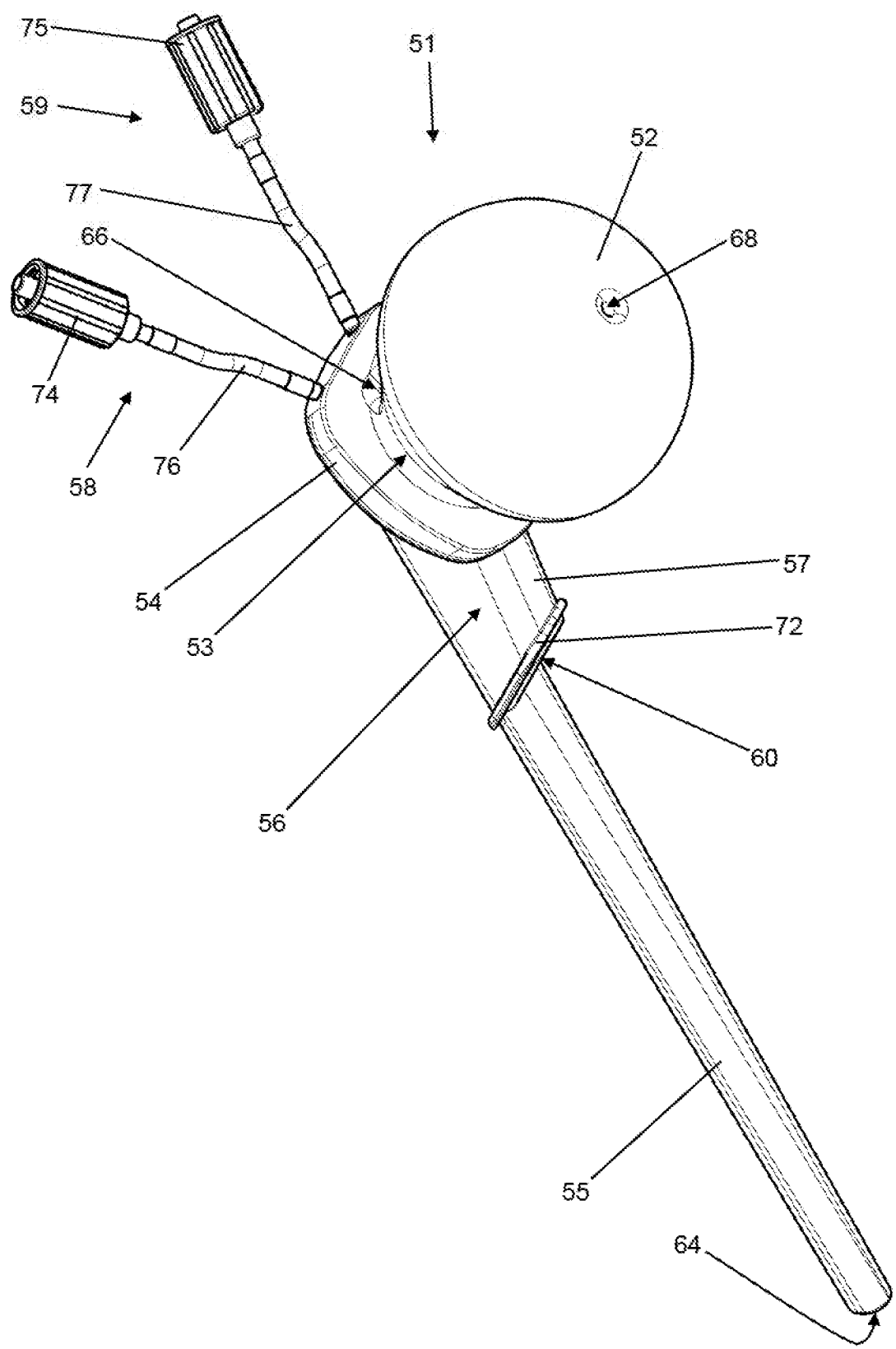
FIG. 7 is a schematic perspective external view of a second exemplary hip joint spacer according to the invention with an irrigation device.
Figure 8:
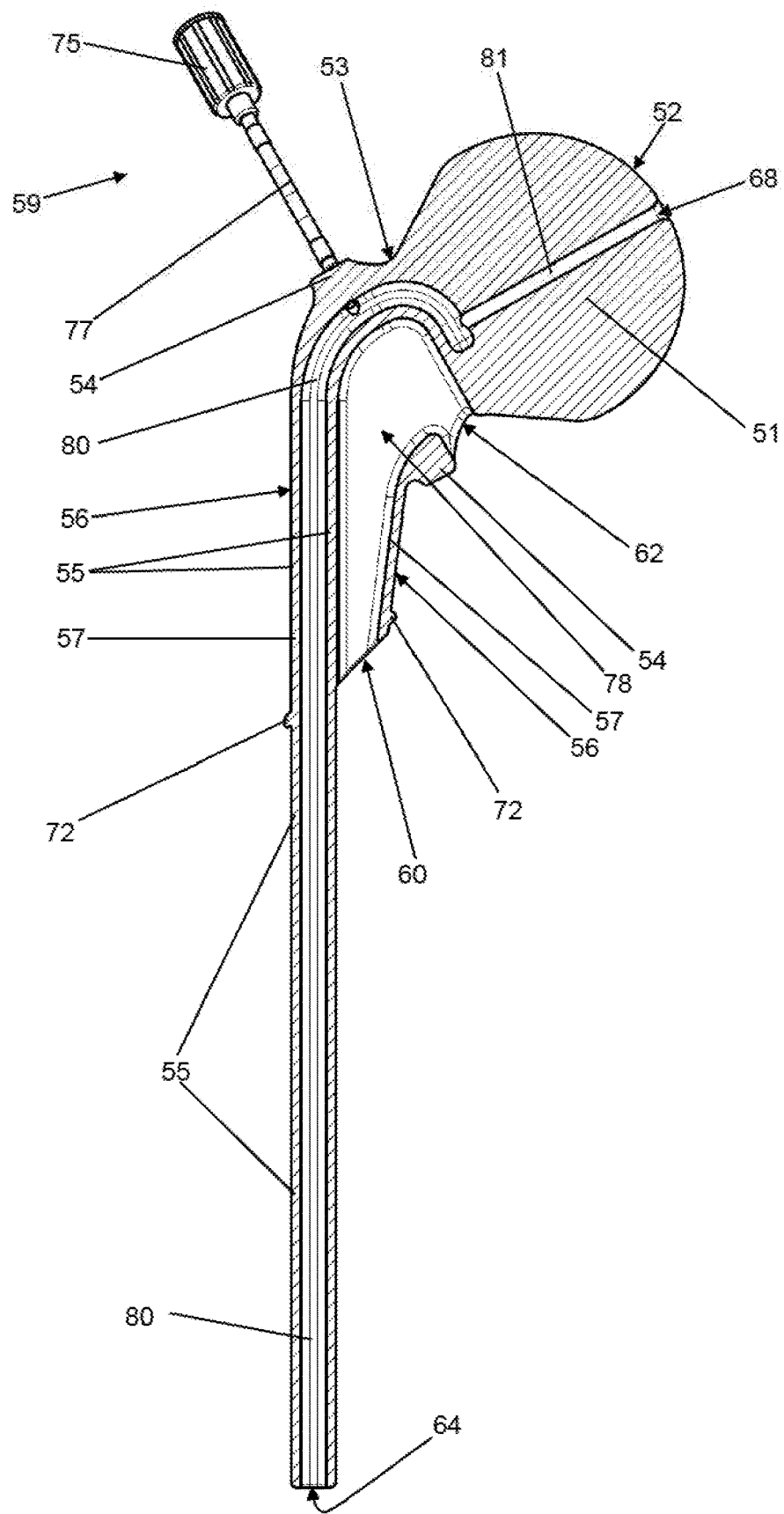
FIG. 8 is a schematic cross-sectional view of the second hip joint spacer according to the invention illustrated in FIG. 7.
Figure 9:
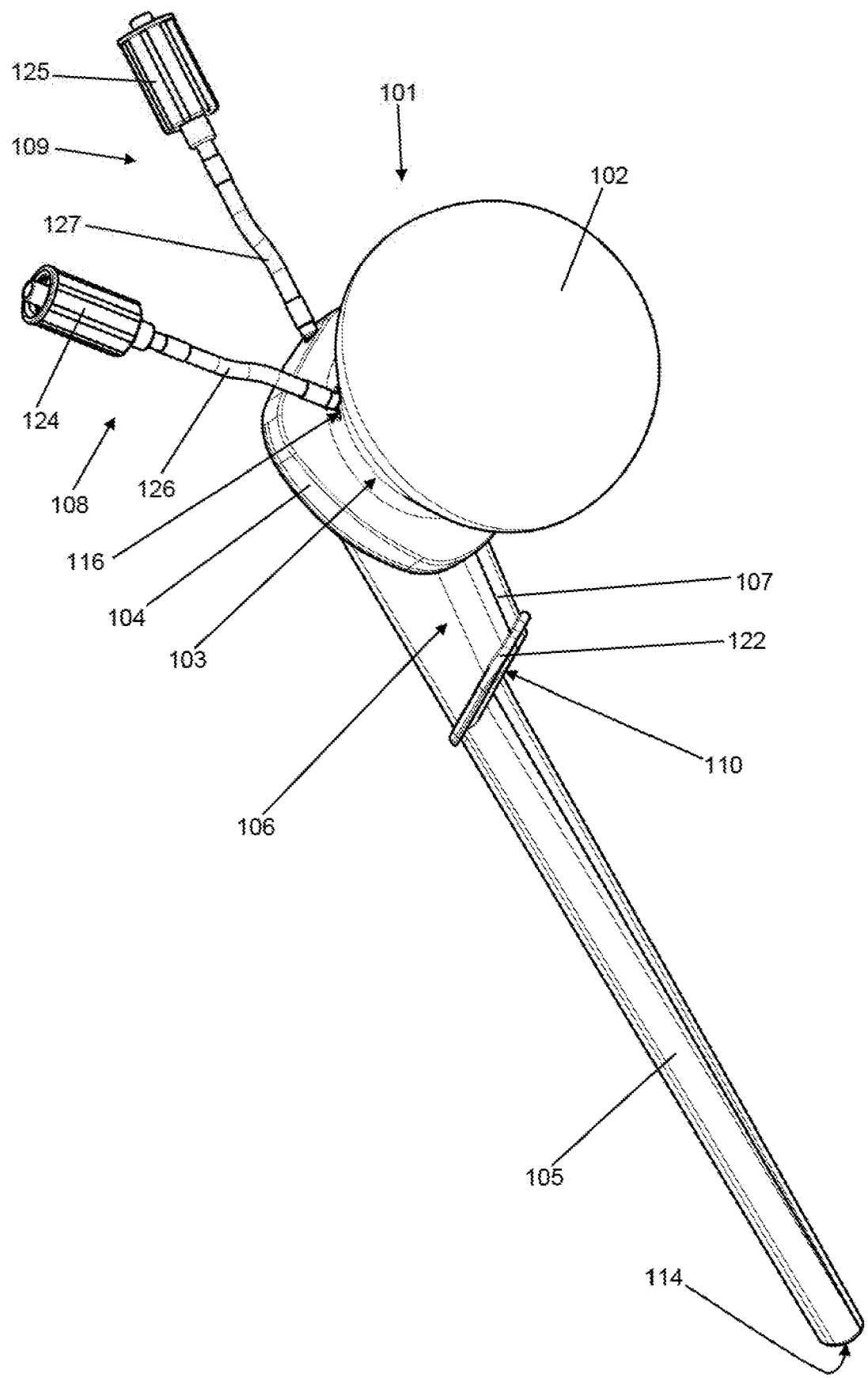
FIG. 9 is a schematic perspective external view of a third exemplary hip joint spacer according to the invention with an irrigation device.
Figure 10:
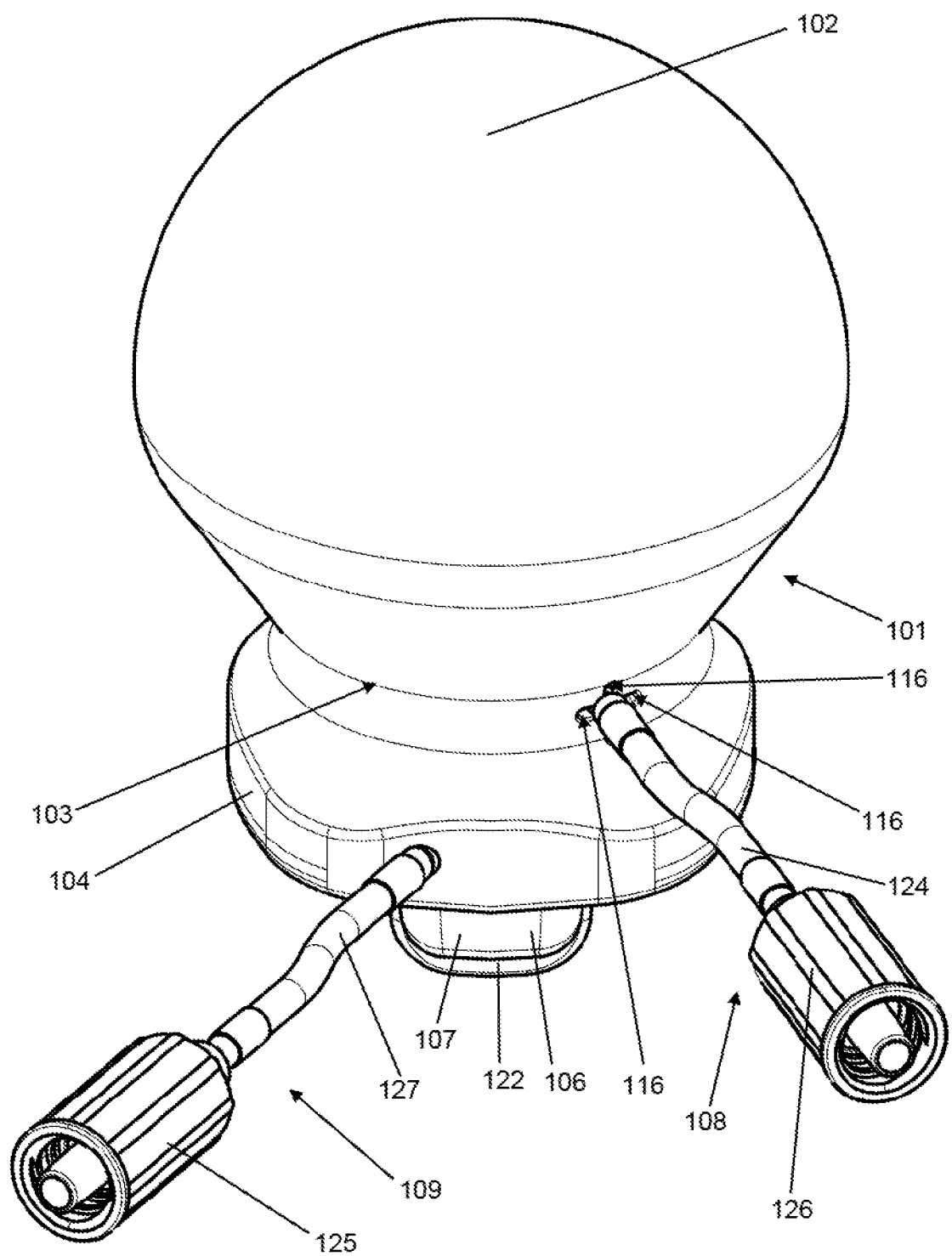
FIG. 10 is a further schematic external view of the third hip joint spacer according to the invention illustrated in FIG. 9.
Figure 11:
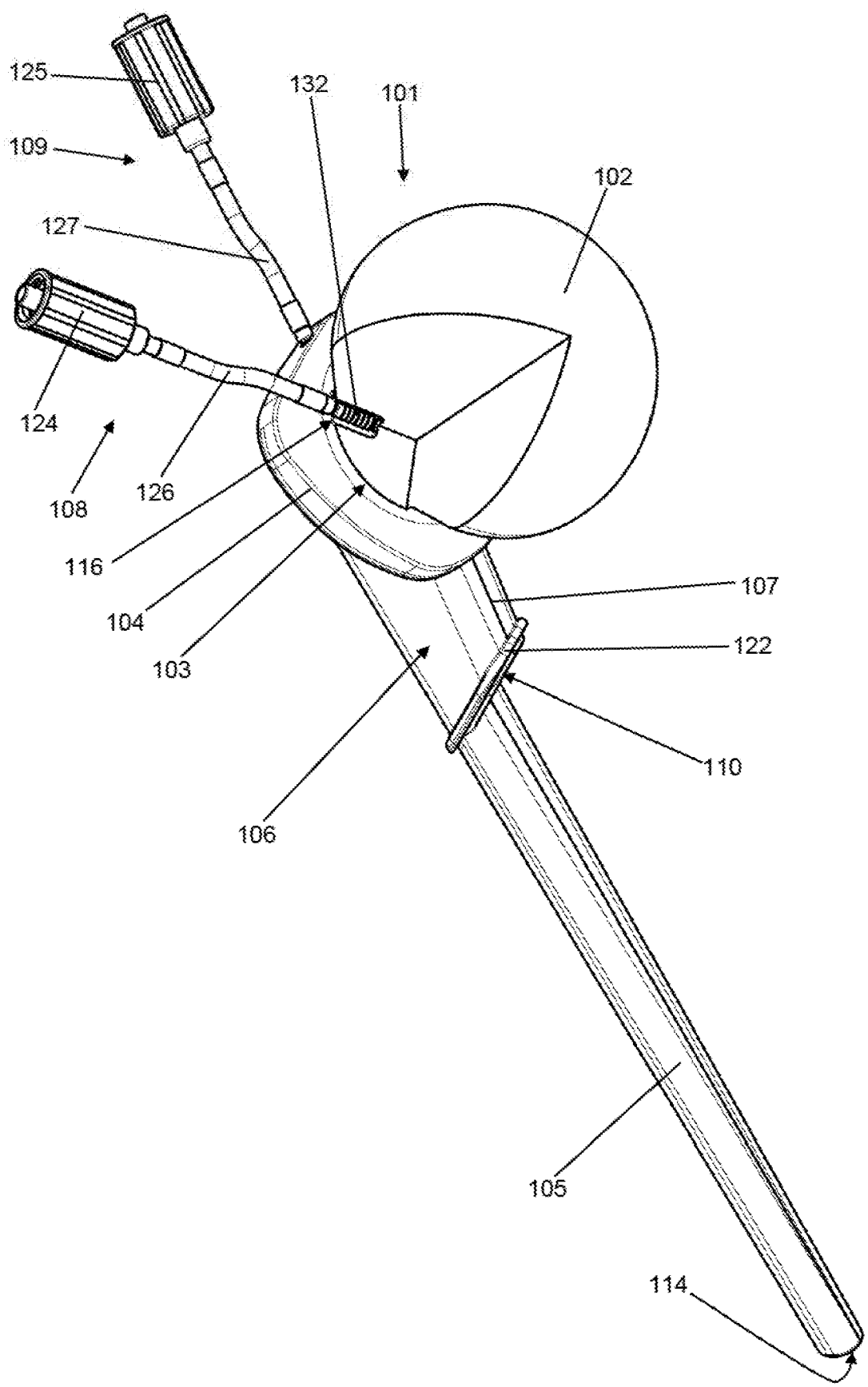
FIG. 11 is a schematic partial sectional view of the third hip joint spacer according to the invention illustrated in FIGS. 9 and 10.

FIGS. 7 and 8 show depictions of a second exemplary embodiment of a hip joint spacer according to the invention with an irrigation device. The second exemplary embodiment largely corresponds to the first exemplary embodiment. The femoral hip joint spacer has a ball head 51 with a sliding surface 52 on the proximal side. The sliding surface 52 may rest when inserted against the hip joint socket and thereby form a part of the hip joint. On the distal side opposite the sliding surface 52, the ball head 51 may be connected to a collar 54 via a neck 53. The neck 53 is preferably thinner than the ball head 51 and the collar 54. On the distal side of the collar 54 a stem 55 may be attached, which extends in the distal direction. In order to fasten the hip joint spacer in the femur, a circumferential fastening area 56 may be provided on an anchoring sleeve 57, which surrounds or respectively encloses the stem 55 on its proximal side. With the circumferential fastening area 56, a connection of the hip joint spacer in a canal of a femur may be effected with the aid of bone cement paste as the "adhesive". The ball head 51, the neck 53, the collar 54, the stem 55 and the anchoring sleeve 57 may form a prosthesis body of the hip joint spacer. The prosthesis body largely corresponds in its external shape to the external shape of known hip joint spacers, apart from the anchoring sleeve 57.

Unlike with known hip joint spacers, on one side of the second exemplary hip joint spacer a first tubular connector 58 may be fastened to an irrigation liquid outlet opening and a second tubular connector 59 may be fastened to an irrigation liquid inlet opening. The irrigation liquid inlet opening and the irrigation liquid outlet opening may lead into the inside of the prosthesis body and be arranged on the collar 54. The first tubular connector 58 and the second tubular connector 59 may be liquid-permeable, such that a medical irrigation liquid may be passed through the second tubular connector 59 into the prosthesis body and a liquid may be drained out of the prosthesis body through the first tubular connector 58. The first connector 58 may be detachably connected to the irrigation liquid outlet opening and the second connector 59 may be detachably connected to the irrigation liquid inlet opening.

The anchoring sleeve 57 may have a distal opening 60 which points in the direction of the distal end of the stem 55, and may have a proximal opening 62 which leads in the direction of the ball head 51. The proximal opening 62 may stretch from the collar 54 right into the neck 53.

At the distal end of the stem 55 a first irrigation liquid discharge opening 64 may be arranged and on the neck 53 an irrigation liquid intake opening 66 may be arranged.

Unlike the first exemplary embodiment illustrated in FIGS. 1 to 6, a second irrigation liquid discharge opening 68 is provided in the center of the sliding surface 52 of the ball head 51. The anchoring sleeve 57 may be arranged between the first irrigation liquid discharge opening 64 and the irrigation liquid intake opening 66.

The fastening area 56 may be delimited on the distal side by a circumferential crosspiece 72 and on the proximal side of the fastening area 56 by the collar 54. The crosspiece 72 may extend up out of the surface of the anchoring sleeve 57 and delimit the anchoring sleeve 57 on its distal side. The crosspiece 72 may be construed to be part of the prosthesis body. The aforementioned crosspiece 72 and the collar 54 may prevent bone cement paste from penetrating, or at least hinder the paste from penetrating, outside the fastening area 56 on fastening of the hip joint spacer to the femur and thereby closing or impeding the first irrigation liquid discharge opening 64, the irrigation liquid intake opening 66, the second irrigation liquid discharge opening 68, the irrigation liquid inlet opening and the irrigation liquid outlet opening or respectively undesirably cementing firm the first connector 58 or the second connector 59 on the prosthesis body. The collar 54 may be designed as a crosspiece protruding from the proximal end of the anchoring sleeve 57 so that the circumferential fastening area 56 is delimited on the proximal side and on the distal side by a protruding crosspiece.

The first connector 58 may have a luer lock adapter 74 and a short, flexible hose 76. The second connector 59 may likewise have a luer lock adapter 75 and a short, flexible hose 77. In this way, the hip joint spacer may be connected by the second connector 59 via the luer lock adapter 75 to a source of a medical irrigation liquid with a pump (not shown) and the first connector 58 may be connected via the luer lock adapter 74 to a collecting vessel and optionally likewise a pump (not shown).

In the cross-sectional view according to FIG. 8, a cavity 78 can be seen, which may be delimited by the internal walls of the anchoring sleeve 57 and the external walls of the stem 55 inside the anchoring sleeve 57. The cavity 78 may connect the distal opening 60 to the proximal opening 62. As a result, the irrigation liquid may flow out of the first irrigation liquid discharge opening 64, subsequently flow along the surface of the stem 55, then flow through the distal opening 60 into the cavity 78, through the cavity 78 and flow out the proximal opening 62 and flow from there over the surface of the neck 53 and of the ball head 51 to the irrigation liquid intake opening 66. The used irrigation liquid may subsequently be sucked in through the irrigation liquid intake opening 66 back into the prosthesis body. A second irrigation liquid circuit may be produced between the second irrigation liquid discharge opening 68 and the irrigation liquid intake opening 66. Thanks to the anchoring sleeve 57 having the cavity 78 which is open on two sides at the distal opening 60 and the proximal opening 62, the medical irrigation liquid may therefore reach the surface of the prosthesis body both on the stem 55 and on the ball head 51 from the first irrigation liquid discharge opening 64 at the distal end of the stem 55. As a result, the connection of the two sides via the cavity 78 ensures that an exchange of liquid is possible on both sides of the prosthesis body. This prevents a malfunction and makes possible uniform treatment. At the same time, the anchoring sleeve 57 and the fastening area 56 may be completely used for cementing, i.e., for anchoring the hip joint spacer in a canal of a femur and thus make possible a particularly robust connection with the femur.

In the cross-sectional view according to FIG. 8, it is further apparent how the irrigation liquid inlet opening can be connected to the first irrigation liquid discharge opening 64 and to the second irrigation liquid intake opening 68 by a duct 80 inside the prosthesis body. To this end, a T-piece duct 81 is provided, which forms a branch from the irrigation liquid inlet opening to the first irrigation liquid discharge opening 64 and the second irrigation liquid discharge opening 68. The stem 55 forms a hollow cylinder. As can be very clearly seen in particular in FIG. 8, the free duct cross-section of the cavity 78 may be approximately three times larger than the free duct cross-section of the duct 80. Similarly, the irrigation liquid intake opening 66 may be connected inside the prosthesis body by a separate second duct (not shown) to the irrigation liquid outlet opening.

The prosthesis body may be made substantially of a plastic material, preferably of a bone cement, such as a PMMA plastic which may be loaded with an antibiotic or with a plurality of antibiotics.

The duct 80 may establish a liquid-permeable connection between the irrigation liquid inlet opening and the first irrigation liquid discharge opening 64 and the second irrigation liquid discharge opening 68. The duct 80 and the separate second duct, which connects the irrigation liquid intake opening 66 inside the prosthesis body to the irrigation liquid outlet opening, may be separated from one another inside the prosthesis body, so that no fluid connection exists between the duct 80 and the second duct inside the prosthesis body.

A coupling element may be arranged on the hose 77 of the second connector 59, which coupling element makes possible a detachable connection of the hose 77 to a coupling in the irrigation liquid inlet opening. A fluid-tight connection to the irrigation liquid inlet opening may be produced with the coupling element.

A valve element (not shown) may be provided in the second duct, directly in front of the irrigation liquid outlet opening, the valve element allowing outflow of liquid from the second duct through the irrigation liquid outlet opening out of the prosthesis body into the first connector 58 and preventing backflow from the first connector 58 into the second duct. The first connector 58 may be connected to the irrigation liquid outlet opening via a detachable connecting element.

A valve element (not shown) may be provided in the duct 80, directly in front of the irrigation liquid inlet opening, the valve element allowing inflow of the medical irrigation liquid into the duct 80 through the irrigation liquid inlet opening into the prosthesis body and preventing backflow from the duct 80 into the second connector 59. The second connector 59 may be connected via the coupling element to a coupling in the irrigation liquid inlet opening.

The first connector 58 and the second connector 59 may be detached from the prosthesis body by pulling away or unscrewing. To this end, liquid-permeable mating fastening elements may be provided in the ducts 80 in the prosthesis body. The mating fastening elements may for example be made from sleeves with internal threads, into which the respective coupling element having an external thread has been or may be screwed.

In the inserted state, the femoral hip joint spacer may be used as follows for irrigation: a medical irrigation liquid with a composition adapted to the patient's needs, such as for example a sterile Ringer's solution with a mixture of suitable antibiotics, is fed through the second connector 59 into the prosthesis body. The medical irrigation liquid may flow through the hose 77 and through the duct 80 through the prosthesis body and exit through the first irrigation liquid discharge opening 64 at the distal end of the stem 55 and through the second irrigation liquid discharge opening 68 at the proximal end of the sliding surface 52 from the prosthesis body. The irrigation liquid may subsequently flow along the surface of the hip joint spacer from the first irrigation liquid discharge opening 64 through the cavity 78 in the anchoring sleeve 57 to the irrigation liquid intake opening 66 as well as from the second irrigation liquid discharge opening 68 around the ball head 51 to the irrigation liquid intake opening 66. The regions therebetween may be irrigated with a film of the medical irrigation liquid. The used irrigation liquid may re-enter the prosthesis body at the irrigation liquid intake opening 66 and flow through the separate second duct to the irrigation liquid outlet opening. From there it may be removed by suction from the prosthesis body through the first connector 58 and the used irrigation liquid may subsequently be disposed of or collected.

If no further irrigation is to take place, the connectors 58, 59 may be separated from the prosthesis body and the remaining hip joint spacer may also be used like a normal hip joint spacer. Provision may preferably be made for the irrigation liquid inlet opening and the irrigation liquid outlet opening to close automatically on pulling or screwing the connectors 58, 59 off the prosthesis body.

FIGS. 9 to 12 show depictions of a third exemplary embodiment of a hip joint spacer according to the invention with an irrigation device. The third exemplary embodiment largely corresponds to the first exemplary embodiment. The femoral hip joint spacer has a ball head 101 with a sliding surface 102 on the proximal side. The sliding surface 102 may rest when inserted against the hip joint socket and thereby form a part of the hip joint. On the distal side opposite the sliding surface 102, the ball head 101 may be connected to a collar 104 via a neck 103. The neck 103 is preferably thinner than the ball head 101 and the collar 104. On the distal side of the collar 104 a stem 105 may be attached, which extends in the distal direction. In order to fasten the hip joint spacer in the femur, a circumferential fastening area 106 may be provided on an anchoring sleeve 107, which surrounds or respectively encloses the stem 105 on its proximal side. With the circumferential fastening area 106, a connection of the hip joint spacer in a canal of a femur may be effected with the aid of bone cement paste as the "adhesive". The ball head 101, the neck 103, the collar 104, the stem 105 and the anchoring sleeve 107 may form a prosthesis body of the hip joint spacer. The prosthesis body largely corresponds in its external shape to the external shape of known hip joint spacers, apart from the anchoring sleeve 107.

Figure 12:
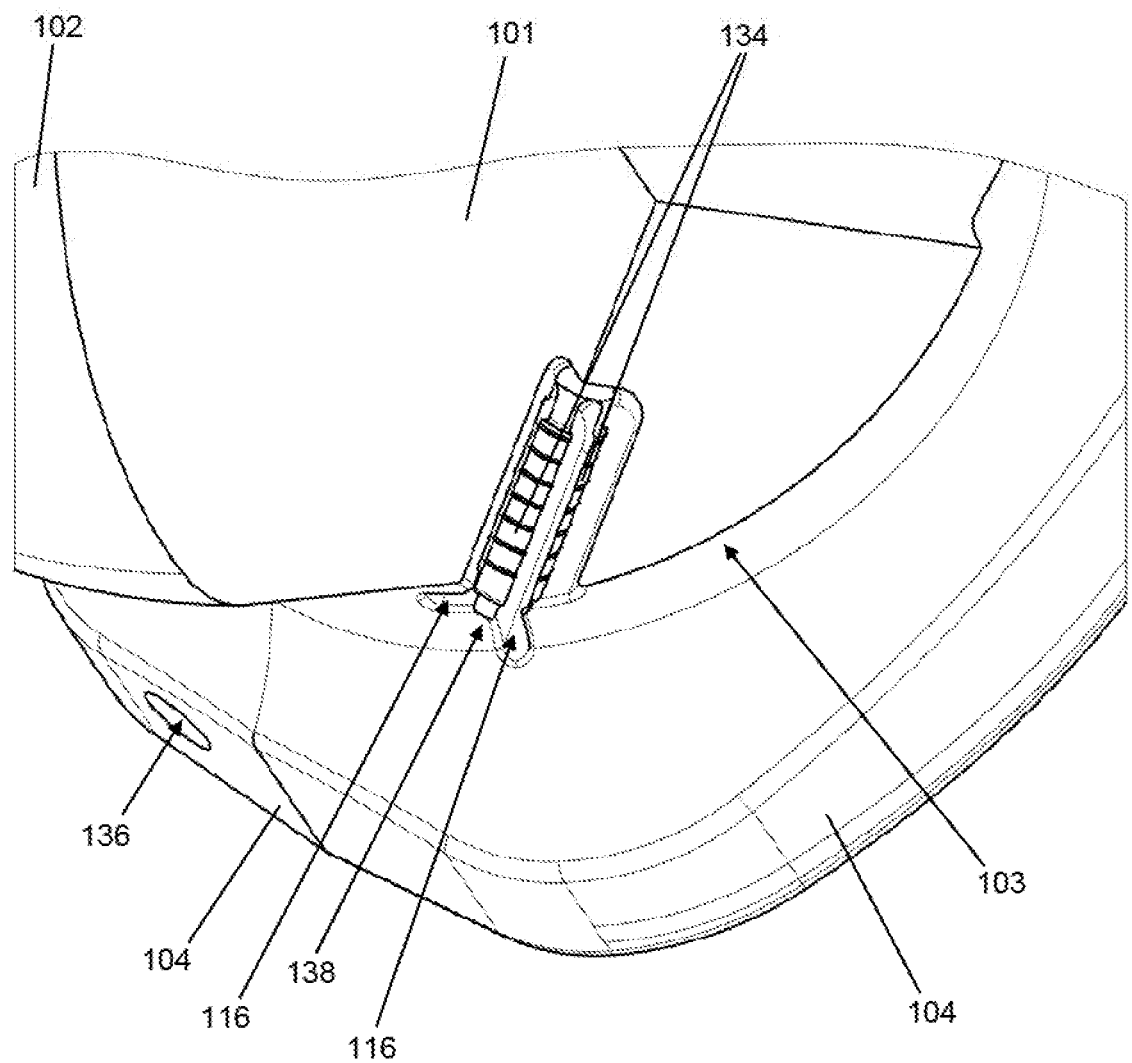
FIG. 12 is a section enlargement of a schematic partial sectional view of a part of the collar, the neck and the ball head of the third hip joint spacer according to the invention illustrated in FIGS. 9 to 11.

Unlike with known hip joint spacers, on one side of the third exemplary hip joint spacer a first tubular connector 108 may be fastened to an irrigation liquid outlet opening 138 and a second tubular connector 109 may be fastened to an irrigation liquid inlet opening 136 (see FIG. 12). The irrigation liquid inlet opening 136 may lead into the inside of the prosthesis body and be arranged on the collar 104. On the other hand, unlike the first two exemplary embodiments, the irrigation liquid outlet opening 138 may be a blind hole in the region of the neck 103. A coupling 134 for fastening a coupling element 132 to the first connector 108 may be provided in the blind hole. The first tubular connector 108 and the second tubular connector 109 may be liquid-permeable, such that a medical irrigation liquid may be passed through the second tubular connector 109 into the prosthesis body and a liquid may be drained out of the blind hole through the first tubular connector 108. The first connector 108 may be detachably connected to the irrigation liquid outlet opening 138 and the second connector 109 may be detachably connected to the irrigation liquid inlet opening 136.

The anchoring sleeve 107 may have a distal opening 110 which points in the direction of the distal end of the stem 105, and may have a proximal opening (similarly to the first two exemplary embodiments) which leads in the direction of the ball head 101. The proximal opening may stretch from the collar 104 right into the neck 103.

At the distal end of the stem 105 an irrigation liquid discharge opening 114 may be arranged and on the neck 103 an irrigation liquid intake opening 116 may be arranged. The irrigation liquid intake opening 116 is to be construed to be a triple star-shaped extension of the irrigation liquid outlet opening 138. The irrigation liquid is sucked in therewith from the surface of the neck 103 into the same blind hole from which it is also removed by suction through the first connector 108 which is fastened in the irrigation liquid outlet opening 138. As a result, the formation of a duct which connects the irrigation liquid outlet opening 138 to the irrigation liquid intake opening 116 may be avoided inside the prosthesis body. The anchoring sleeve 107 may be arranged between the irrigation liquid discharge opening 114 and the irrigation liquid intake opening 116.

The fastening area 106 may be delimited on the distal side by a circumferential crosspiece 122 and on the proximal side of the fastening area 106 by the collar 104. The crosspiece 122 may extend up out of the surface of the anchoring sleeve 107 and delimit the anchoring sleeve 107 on its distal side. The crosspiece 122 may be construed to be part of the prosthesis body. The aforementioned crosspiece 122 and the collar 104 may prevent bone cement paste from penetrating, or at least hinder the paste from penetrating, outside the fastening area 106 on fastening of the hip joint spacer to the femur and thereby closing or respectively impeding the irrigation liquid discharge opening 114, the irrigation liquid intake opening 116, the irrigation liquid inlet opening 136 and the irrigation liquid outlet opening 138 or respectively undesirably cementing firm the first connector 108 or the second connector 109 on the prosthesis body. The collar 104 may be designed as a crosspiece protruding from the proximal end of the anchoring sleeve 107 so that the circumferential fastening area 106 is delimited on the proximal side and on the distal side by a protruding crosspiece.

The first connector 108 may have a luer lock adapter 124 and a short, flexible hose 126. The second connector 109 may likewise have a luer lock adapter 125 and a short, flexible hose 127. In this way, the hip joint spacer can be connected by the second connector 109 via the luer lock adapter 125 to a source of a medical irrigation liquid with a pump (not shown) and the first connector 108 may be connected via the luer lock adapter 124 to a collecting vessel and optionally likewise a pump (not shown).

The inner construction of the third exemplary embodiment corresponds to the cross-section of the first exemplary embodiment, which is shown in FIG. 4. A cavity may therefore be provided inside the anchoring sleeve 107 (which corresponds to the cavity 28 according to the first exemplary embodiment (see FIG. 4)), which may be delimited by the internal walls of the anchoring sleeve 107 and the external walls of the stem 105 inside the anchoring sleeve 107. The cavity may connect the distal opening 110 to the proximal opening. As a result, the irrigation liquid may flow out of the irrigation liquid discharge opening 114, subsequently flow along the surface of the stem 105, then flow through the distal opening 110 into the cavity, through the cavity and flow out the proximal opening and flow from there over the surface of the neck 103 and of the ball head 101 to the irrigation liquid intake opening 116. The used irrigation liquid may subsequently be sucked in through the irrigation liquid intake opening 116 back into the prosthesis body. Thanks to the anchoring sleeve 107 having the cavity which is open on two sides at the distal opening 110 and the proximal opening 112, the medical irrigation liquid may therefore reach the surface of the prosthesis body both on the stem 105 and on the ball head 101. As a result, it is sufficient to provide one irrigation liquid discharge opening 114 and one irrigation liquid intake opening 116, in order to be able to reach the surfaces of the prosthesis body which are achievable with the medical irrigation liquid and to be able to treat them therewith. If there is more than one irrigation liquid discharge opening 114 and more than one irrigation liquid intake opening 116, however, the connection of the two sides via the cavity ensures that an exchange of liquid is possible on both sides of the prosthesis body. This prevents a malfunction and makes possible uniform treatment. At the same time, the anchoring sleeve 107 and the fastening area 106 may be completely used for cementing, i.e., for anchoring the hip joint spacer in a canal of a femur and thus make possible a particularly robust connection with the femur.

Similarly to the cross-sectional view according to FIG. 4, the irrigation liquid inlet opening 136 may be connected to the irrigation liquid discharge opening 114 inside the prosthesis body via a duct inside the stem 105. The stem 105 forms a hollow cylinder. The free duct cross-section of the cavity may be approximately larger than, in particular at least double the size of, the free duct cross-section of the duct.

The prosthesis body may be made substantially of a plastic material, preferably of a bone cement, such as a PMMA plastic which may be loaded with an antibiotic or with a plurality of antibiotics.

The duct may establish a liquid-permeable connection between the irrigation liquid inlet opening 136 and the irrigation liquid discharge opening 114. The duct may be separated inside the prosthesis body from the blind hole of the irrigation liquid outlet opening 138 so that no fluid connection exists between the duct and the irrigation liquid outlet opening 138 inside the prosthesis body.

The coupling element 132 may be arranged on the hose 126 of the first connector 108, which coupling element makes possible a detachable connection of the hose 126 to the irrigation liquid outlet opening 138. A fluid-tight connection to the irrigation liquid inlet opening 138 may be produced with the coupling element 132.

A valve element (not shown) can be provided in the duct, directly in front of the irrigation liquid inlet opening 136, the valve element allowing inflow of the medical irrigation liquid into the duct through the irrigation liquid inlet opening 136 into the prosthesis body and preventing backflow from the duct into the second connector 109. The first connector 108 may be connected via the coupling element 132 to the irrigation liquid inlet opening 136.

The first connector 108 and the second connector 109 may be detached from the prosthesis body by pulling away or unscrewing. To this end, liquid-permeable mating fastening elements may be provided in the prosthesis body. The mating fastening elements may for example be made from sleeves with internal threads as the coupling 134, into which the coupling element 132 having an external thread has been or may be screwed.

In the inserted state, the femoral hip joint spacer may be used as follows for irrigation: a medical irrigation liquid with a composition adapted to the patient's needs, such as for example a sterile Ringer's solution with a mixture of suitable antibiotics, is fed through the second connector 109 into the prosthesis body. The medical irrigation liquid may flow through the hose 127 and through the duct through the prosthesis body and exit through the irrigation liquid discharge opening 114 at the distal end of the stem 105 out of the prosthesis body. The irrigation liquid may subsequently flow along the surface of the hip joint spacer from the first irrigation liquid discharge opening 114 through the cavity in the anchoring sleeve 107 to the irrigation liquid intake opening 116. The regions therebetween may be irrigated with a film of the medical irrigation liquid. The used irrigation liquid may re-enter the prosthesis body at the irrigation liquid intake opening 116 and may be removed by suction through the irrigation liquid outlet opening 138 and through the first connector 108 from the prosthesis body and the used irrigation liquid may subsequently be disposed of or collected.

If no further irrigation is to take place, the connectors 108, 109 may be separated from the prosthesis body and the remaining hip joint spacer may also be used like a normal hip joint spacer. Provision may preferably be made for the irrigation liquid inlet opening and the irrigation liquid outlet opening to close automatically on pulling or screwing the connectors 108, 109 off the prosthesis body.

The stem 5, 55, 105 and the ball head 1, 51, 101 may, according to an alternative embodiment, be screwed onto one another by a threaded rod having an external thread.

The use of a PMMA mixed with antibiotics or antimycotics or other pharmaceutically active substances at least as an external layer on hip joint spacers according to the invention has the advantage that a particularly large quantity of the active ingredients is available initially over a large area. In addition, a particular combinatorial effect results, namely that circulation of the medical irrigation liquid promotes and enhances release of the active ingredients at the surface of the hip joint spacer.

Although illustrated and described above with reference to certain specific embodiments and examples, the present disclosure is nevertheless not intended to be limited to the details shown. Rather, various modifications may be made in the details within the scope and range of equivalents of the claims and without departing from the spirit of the disclosure. The features of the invention disclosed in the above description, as well as in the claims, figures and exemplary embodiments, may be essential both individually and in any desired combination to realization of the invention in its various embodiments.

What is claimed:

1. A femoral hip joint spacer for temporary replacement of a part of a hip joint, the hip joint spacer comprising:
   a prosthesis body having a ball head with a surface including both an irrigation liquid inlet opening and an irrigation liquid outlet opening, a neck with a proximal side connected to the ball head and a distal side which is opposite the ball head, a stem connected to the neck on the distal side of the neck and including both a proximal side and a distal side, and an anchoring sleeve connected to the stem including both a proximal side and a distal side and enclosing the stem on the proximal side of the stem with a circumferential fastening area, wherein
   the distal side of the stem includes at least one irrigation liquid discharge opening and either the ball head or the neck includes at least one irrigation liquid intake opening,
   the at least one irrigation liquid discharge opening is connected inside the prosthesis body in a liquid-permeable manner to the irrigation liquid inlet opening and is not connected inside the prosthesis body in a liquid-permeable manner to the irrigation liquid outlet opening, and
   the at least one irrigation liquid intake opening is connected inside the prosthesis body in a liquid-permeable manner to the irrigation liquid outlet opening and is not connected inside the prosthesis body in a liquid-permeable manner to the irrigation liquid inlet opening, and
   the anchoring sleeve includes a cavity formed inside the anchoring sleeve which is open on two sides, the cavity connecting the proximal side of the anchoring sleeve to the distal side of the anchoring sleeve in a liquid-permeable manner.

2. The hip joint spacer according to claim 1, further comprising a first tubular and liquid-permeable connector for draining medical irrigation liquid from the prosthesis body, wherein the first connector is connected or connectable in a liquid-permeable manner to the irrigation liquid outlet opening, and a second tubular and liquid-permeable connector for feeding the medical irrigation liquid into the prosthesis body, wherein the second connector is connected or connectable in a liquid-permeable manner to the irrigation liquid inlet opening.

3. The hip joint spacer according to claim 1, wherein the at least one irrigation liquid discharge opening and the at least one irrigation liquid intake opening are arranged in the surface of the prosthesis body outside the circumferential fastening area.

4. The hip joint spacer according to claim 1, wherein the neck has a lateral side and the irrigation liquid inlet opening, the irrigation liquid outlet opening, or both the irrigation liquid inlet opening and the irrigation liquid outlet opening is or are arranged on the lateral side of the neck of the prosthesis body.

5. The hip joint spacer according to claim 1, wherein the stem has a hollow cylinder-shape and a duct formed inside the stem which connects the at least one irrigation liquid discharge opening to the at least one irrigation liquid inlet opening in a liquid-permeable manner.

6. The hip joint spacer according to claim 1, wherein
   the fastening area is delimited for accommodating bone cement paste, or
   the fastening area is delimited by a first circumferential crosspiece extending up out of the surface of the prosthesis body on the proximal side of the anchoring sleeve and a second circumferential crosspiece extending up out of the surface of the prosthesis body on the distal side of the anchoring sleeve, the fastening area accommodating bone cement paste within the crosspieces, or
   the fastening area is delimited by one circumferential crosspiece extending up out of the surface of the prosthesis body on the distal side of the anchoring sleeve and one circumferential collar extending up out of the surface of the prosthesis body on the proximal side of the anchoring sleeve, the fastening area accommodating bone cement paste within the crosspiece and the collar.

7. The hip joint spacer according to claim 1, wherein one of the at least one irrigation liquid discharge opening is arranged at the distal side of the stem, the ball head has a proximal side with a second irrigation liquid discharge opening inside the prosthesis body, and the one of the at least one irrigation liquid discharge opening and the second irrigation liquid discharge opening are connected to the irrigation liquid inlet opening in a liquid-permeable manner.

8. The hip joint spacer according to claim 1, wherein the ball head has a distal side and the at least one irrigation liquid intake opening is arranged on the neck of the prosthesis body, on the distal side of the ball head, or both on the neck of the prosthesis body and on the distal side of the ball head.

9. The hip joint spacer according to claim 1, wherein the anchoring sleeve is arranged between the at least one irrigation liquid discharge opening and the at least one irrigation liquid intake opening so that, when the circumferential fastening area is closed in a liquid-tight manner, irrigation liquid may only flow through the cavity which is open on two sides from the at least one irrigation liquid discharge opening to the at least one irrigation liquid intake opening.

10. The hip joint spacer according to claim 1, further comprising a first self-sealing coupling arranged at the irrigation liquid inlet opening inside or on the surface of the prosthesis body, a second self-sealing coupling arranged at the irrigation liquid outlet opening inside or on the surface of the prosthesis body, a first connector detachably connected or connectable to the irrigation liquid inlet opening, and a second connector detachably connected or connectable to the irrigation liquid outlet opening.

11. The hip joint spacer according to claim 1, wherein the sum of the cross-sectional areas of all of the at least one irrigation liquid intake opening together is at least as great as the cross-sectional area of the irrigation liquid inlet opening, or the sum of the cross-sectional areas of all of the at least one irrigation liquid discharge opening is at least as great as the cross-sectional area of the irrigation liquid outlet opening.

12. The hip joint spacer according to claim 1, further comprising:
   a first valve arranged in a first duct within the prosthesis body which connects the at least one irrigation liquid intake opening to the irrigation liquid outlet opening in a liquid-permeable manner, the first valve being openable solely by applying a vacuum at the irrigation liquid outlet opening and preventing backflow of irrigation liquid into the first duct, or
   a second valve arranged in a second duct within the prosthesis body which connects the at least one irrigation liquid discharge opening to the irrigation liquid inlet opening in a liquid-permeable manner, the second valve being openable solely by applying a vacuum at the irrigation liquid inlet opening and preventing backflow of the irrigation liquid into the second duct.

13. The hip joint spacer according to claim 1, wherein the cavity of the anchoring sleeve has a free duct cross-section, the stem has a longitudinal axis and an outer lateral surface and a free duct cross-section, the anchoring sleeve has an internal wall, and the free duct cross-section of the cavity is as large as or larger than the free duct cross-section of the stem or the cavity extends at least in part parallel to the longitudinal axis of the stem and is delimited by the outer lateral surface of the stem and the internal wall of the anchoring sleeve.

14. The hip joint spacer according to claim 1, wherein the stem has a longitudinal axis and the anchoring sleeve has a closed lateral surface or the anchoring sleeve has a notch arranged parallel to the longitudinal axis of the stem.

15. The hip joint spacer according to claim 1, wherein the ball head has a distal side and the hip joint spacer further comprises a collar arranged on the distal side of the ball head and distally from the irrigation liquid inlet opening and the irrigation liquid outlet opening as well as between the ball head and the anchoring sleeve, wherein the collar runs around the proximal side of the anchoring sleeve.

16. The hip joint spacer according to claim 1, wherein the anchoring sleeve has an outer lateral surface that either includes a rubbery-elastic coating or is structured for press-fit anchoring or for anchoring polymethyl methacrylate bone cement.

17. The hip joint spacer according to claim 1, wherein the anchoring sleeve tapers in the distal direction.

18. The hip joint spacer according to claim 1, further comprising a hollow cylinder-shaped rubbery elastic sleeve with a collar on the proximal side of the elastic sleeve, the elastic sleeve forming a sheath over the anchoring sleeve.

19. The hip joint spacer according to claim 1, wherein one of the at least one irrigation liquid intake opening is formed as the irrigation liquid outlet opening, and the hip joint spacer further comprises a fastener for detachably connecting a tubular and liquid-permeable connector for draining irrigation liquid from the prosthesis body arranged in the irrigation liquid intake opening, wherein the irrigation liquid outlet opening cannot be closed by the connected connector.

20. The hip joint spacer according to claim 1, wherein the cavity of the anchoring sleeve is within the prosthesis body and is not connected in a liquid-permeable manner either to the irrigation liquid inlet opening or to the irrigation liquid outlet opening.

* * * * *